United States Patent
Suzuma et al.

(10) Patent No.: US 11,193,910 B2
(45) Date of Patent: Dec. 7, 2021

(54) DEVICE AND METHOD OF DETECTING MAGNETIC CHARACTERISTIC CHANGE FOR LONG MATERIAL

(71) Applicant: NIPPON STEEL CORPORATION, Tokyo (JP)

(72) Inventors: Toshiyuki Suzuma, Tokyo (JP); Yoshiyuki Nakao, Tokyo (JP); Yoshiyuki Ota, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 19 days.

(21) Appl. No.: 16/637,640

(22) PCT Filed: Jun. 29, 2018

(86) PCT No.: PCT/JP2018/024754
§ 371 (c)(1),
(2) Date: Feb. 7, 2020

(87) PCT Pub. No.: WO2019/087460
PCT Pub. Date: May 9, 2019

(65) Prior Publication Data
US 2020/0284758 A1     Sep. 10, 2020

(30) Foreign Application Priority Data

Oct. 30, 2017  (WO) .................. PCT/JP2017/039076

(51) Int. Cl.
*G01N 27/80*   (2006.01)
*G01N 33/204*  (2019.01)

(52) U.S. Cl.
CPC ........... *G01N 27/80* (2013.01); *G01N 33/204* (2019.01)

(58) Field of Classification Search
CPC ................ G01R 33/00; G01R 33/0035; G01R 33/0023; G01R 33/0017; G01R 31/3191;
(Continued)

(56) References Cited

U.S. PATENT DOCUMENTS

| 4,818,935 A | 4/1989 | Takahashi et al. |
| 5,537,037 A | 7/1996 | Otaka et al. |

(Continued)

FOREIGN PATENT DOCUMENTS

| EP | 0 027 368 A2 | 4/1981 |
| JP | 53-142289 A | 12/1978 |

(Continued)

OTHER PUBLICATIONS

International Search Report for PCT/JP2018/024754 dated Sep. 18, 2018.
Tanaka et al., "A discussion for the measuring method of differential permeability", The 57th Joint Conference of Electrical, Electronics and Information Engineers in Kyushu 2004, 04-2P-04, p. 204.

(Continued)

*Primary Examiner* — Patrick Assouad
*Assistant Examiner* — Taqi R Nasir
(74) *Attorney, Agent, or Firm* — Birch, Stewart, Kolasch & Birch, LLP

(57) ABSTRACT

A device of detecting magnetic characteristic change for a long material includes: an exciting coil into which the long material is inserted and which magnetizes the long material in a longitudinal direction; a detecting coil into which the long material is inserted and which detects a magnetic flux generated in the long material due to magnetization by the exciting coil; and a yoke member which has a first opening portion which is positioned on one side of the long material in the longitudinal direction and into which the long material is inserted and a second opening portion which is positioned on the other side of the long material in the longitudinal (Continued)

direction and into which the long material is inserted, and has a shape which is substantially axially symmetrical about an axis passing the first opening portion and the second opening portion, and the exciting coil and the detecting coil are surrounded by the yoke member, the first opening portion, and the second opening portion.

21 Claims, 13 Drawing Sheets

(58) Field of Classification Search
CPC ...... G01N 27/80; G01N 33/204; G01B 7/004; G01C 17/38; G06F 3/017; G06F 3/0346; G06F 3/012
See application file for complete search history.

(56) References Cited

U.S. PATENT DOCUMENTS

| | | | | |
|---|---|---|---|---|
| 5,739,685 A | * | 4/1998 | Suzuma | G01N 27/82 324/225 |
| 5,781,513 A | * | 7/1998 | Fuji | G11B 11/10521 369/100 |

FOREIGN PATENT DOCUMENTS

| | | | | |
|---|---|---|---|---|
| JP | 56-97866 | A | | 8/1981 |
| JP | 61-35348 | A | | 2/1986 |
| JP | 62-6163 | A | | 1/1987 |
| JP | 63-70158 | A | | 3/1988 |
| JP | 2-78948 | A | | 3/1990 |
| JP | 6-324021 | A | | 11/1994 |
| JP | 7-100735 | A | | 4/1995 |
| JP | H07100735 | A * | 4/1995 | ............. G01N 27/72 |
| JP | 2001-133441 | A | | 5/2001 |
| JP | 2002-14081 | A | | 1/2002 |
| JP | 2002014081 | A * | 1/2002 | ............. G01N 27/72 |
| JP | 2005-257701 | A | | 9/2005 |
| JP | 2010-25746 | A | | 2/2010 |
| JP | 2011-203092 | A | | 10/2011 |
| JP | 2011203092 | A * | 10/2011 | |
| JP | 2015-34743 | A | | 2/2015 |

OTHER PUBLICATIONS

Written Opinion of the International Searching Authority for PCT/JP2018/024754 (PCT/ISA/237) dated Sep. 18, 2018.

* cited by examiner $H = nI/2\pi r$
n: NUMBER OF EXCITING COIL WINDINGS $d\phi/dt = V \rightarrow B = \int V dt/S$
S: CROSS-SECTIONAL AREA OF TEST PIECE

< IN BOTH CASES OF B AND H, CLOCKWISE DIRECTION IS POSITIVE DIRECTION >

DEVICE AND METHOD OF DETECTING MAGNETIC CHARACTERISTIC CHANGE FOR LONG MATERIAL

Priority is claimed on PCT/JP2017/039076 filed on Oct. 30, 2017, the content of which is incorporated herein by reference.

BACKGROUND OF THE INVENTION

Field of the Invention

The present invention relates to a device and a method of detecting magnetic characteristic change for a long material, which detect portions where magnetic characteristics change in the long material.

Description of Related Art

It has been known that in a case where poor quenching is partially caused in a heat treatment of a steel pipe (hereinafter, referred to as "pipe") which is an example of a long material, magnetic characteristics change in the part where the poor quenching is performed. Using this characteristic, a state of the heat treatment performed on the pipe can be recognized by measuring the magnetic characteristics of the pipe.

FIG. 1A is a diagram briefly showing a measurement method using a test piece, which has been known as the most usual method of measuring magnetic characteristics of a pipe. FIG. 1B is an example of measurement results (magnetic characteristic curves, BH curve) obtained by the measurement method shown in FIG. 1A.

As shown in FIG. 1A, in this measurement method, an exciting coil 1 and a detecting coil 2 are wound around a test piece TP obtained by cutting a pipe into a short piece in a longitudinal direction of the pipe. In addition, the test piece TP is magnetized by a magnetic field (field intensity H) generated by the exciting coil 1, and a magnetic flux generated in the test piece TP by the magnetization is measured as an induced electromotive force of the detecting coil 2. The induced electromotive force is time-integrated, and then divided by the cross-sectional area of the test piece TP to obtain a magnetic flux density B in the test piece TP. The results shown in FIG. 1B show measurement results of a test piece TP subjected to normal quenching and measurement results of a test piece TP subjected to air cooling (annealing) after the heating, and it is found that the magnetic characteristic curve significantly changes with a difference in the heat treatment. Actual magnetic characteristics of the poorly quenched portion are predicted to be in between magnetic characteristics in a case where normal quenching is performed and magnetic characteristics in a case where annealing is performed. Accordingly, by recognizing a change of the magnetic characteristic curve, a part where magnetic characteristics change due to the heat treatment, such as a poorly quenched portion, can be detected.

Since poor quenching causes a change in the material characteristics such as insufficient hardness, it is desirable to inspect all pipes early. However, in a case of the measurement method shown in HG 1A, pipes are required to be cut into short pieces in a longitudinal direction and the pipes after the cutting cannot be dealt with as products. Accordingly, all pipes cannot be inspected. In inspecting all pipes, it is necessary to perform the measurement in a non-destructive manner Thus, various methods and devices have been proposed to indirectly measure magnetic characteristics of the material.

In addition, in a case where fine poorly quenched portions are distributed in a part of a normal quenched portion such as a part in a circumferential direction of a pipe, if a sensor such as a detecting coil which detects a magnetic flux has a size not sufficiently smaller than the area of the fine poorly quenched portion, magnetic characteristic information acquired by the sensor includes both of magnetic characteristic information of the normal quenched portion and magnetic characteristic information of the poorly quenched portion. Accordingly, it is thought that it is difficult to detect a poorly quenched portion generated in a part of a cross-section based on a difference in the magnetic characteristics between a normal quenched portion and the poorly quenched portion.

For example, Patent Document 1 proposes a device which measures a depth of a quench-hardened layer of a steel material in a non-destructive manner. Specifically, the device described in Patent Document 1 includes an exciting coil which generates a low-frequency alternating-current magnetic field for magnetization in a direction along a surface of a steel material, a detecting coil which detects an induction magnetic field which is induced by an eddy current generated in the steel material, and a calculation unit which stores correlation data between a depth of a known quench-hardened layer of the same kind of steel material and an output voltage in advance and calculates a depth of a quench-hardened layer of the target steel material from an output voltage of the detecting coil and the correlation data, and has a configuration in which the steel material is inserted into both the exciting coil and the detecting coil (see claim 3 and FIG. 7 in Patent Document 1). That is, Patent Document 1 proposes a device using an exciting coil and a detecting coil which are of a so-called encircling coil type.

Patent Document 1 also proposes a configuration in which in a yoke member which is U-shaped when viewed from side and has a pair of parallel contact cores which are brought into contact with a surface of a steel material, an exciting coil is wound around one contact core and a detecting coil is wound around the other contact core (see claim 5 and FIG. 11 in Patent Document 1). That is, Patent Document 1 also proposes a device using a measurement head provided with an external magnetic circuit (yoke member, exciting coil) and a detecting coil.

The device described in FIG. 7 in Patent Document 1 (device using the encircling coil) is similar to the measurement method shown in FIG. 1A in that the exciting coil and the detecting coil are wound in a circumferential direction of the steel material and the steel material is directly magnetized to directly detect a temporal change of the magnetic flux in the steel material by the detecting coil. However, in the encircling exciting coil simple body, the magnetic path of a magnetic flux to be generated is an open magnetic path, and thus the magnetization state of the steel material markedly varies according to the position of an end portion of the steel material in the longitudinal direction. That is, in order to obtain a constant magnetization state, the end portion of the steel material in the longitudinal direction is required to be sufficiently separated from an end portion of the exciting coil. In other words, there is a problem in that a region where the measurement cannot be performed (dead zone) exists in the end portion of the steel material in the longitudinal direction. In order to accurately detect portions where magnetic characteristics change of the material characteristics over the whole length thereof to improve an inspection yield, it is necessary to reduce the dead zone as much as possible.

In addition, in a case where the device (device using the measurement head provided with the external magnetic circuit and the detecting coil) described in FIG. 11 in Patent Document 1 is applied to the detection of portions where magnetic characteristics change of the material characteristics of the pipe which is relatively moved in the longitudinal direction change, there is a concern that a scratch may occur on an outer surface of the pipe in a case where the yoke member (contact core) constituting the external magnetic circuit is brought into contact with the pipe. Therefore, it is necessary to set a clearance (gap between the yoke member and the pipe) of a predetermined or more length. However, in a case where the length of the clearance increases with the variation of pass-line of the pipe, magnetic information of the pipe which is obtained via the magnetic flux is sharply reduced, and thus the value which is measured by the detecting coil dominantly reflects magnetic characteristics of the yoke member substantially. Accordingly, in a case where the variation of pass-line is large, the value which is measured by the detecting coil also varies, and thus there is a problem in that magnetic characteristics of the necessary pipe cannot be accurately detected over the whole length thereof.

Patent Document 2 proposes a method of measuring the hardness of a material in a non-destructive manner by measuring the Barkhausen noise. Specifically, Patent Document 2 describes a method of measuring the hardness of a material in a non-destructive manner by measuring the Barkhausen noise generated by a change in the magnetization caused by applying an increasing or decreasing magnetic field to a ferromagnetic material to be measured, in which a magnetic field strength when the amplitude of the Barkhausen noise reaches the maximum is measured to measure the hardness of the material based on the relationship between the hardness of the ferromagnetic material and the magnetic field strength when the amplitude of the Barkhausen noise reaches the maximum, which has been previously obtained (claim 2 in Patent Document 2).

It has been known that the amplitude of the Barkhausen noise reaches the maximum at a point at which the inclination of a tangent of a magnetic characteristic curve, that is, a differential magnetic permeability reaches the maximum. Accordingly, in the detection of a poorly quenched portion generated in a part of a cross-section using the method described in Patent Document 2, a magnetic field strength is measured at a point at which the differential magnetic permeability reaches the maximum in the magnetic characteristic curve, and thus the hardness of a material is measured. The point at which the differential magnetic permeability reaches the maximum is positioned in the first or third quadrant of the magnetic characteristic curve expressed in an orthogonal coordinate system.

However, as will be described later, it has been found that in a case where the inventors acquire a magnetic characteristic curve by inserting a pipe into an exciting coil and a detecting coil, the position of a point at which the amplitude of the Barkhausen noise reaches the maximum (the differential magnetic permeability reaches the maximum) in the acquired magnetic characteristic curve is substantially constant regardless of the presence or absence of a poorly quenched portion generated in a part of a cross-section. Accordingly, with the method described in Patent Document 2, a poorly quenched portion generated in a part of a cross-section cannot be accurately detected.

Patent Document 3 proposes a method of electromagnetically measuring material characteristics of a magnetic material, in which a differential magnetic permeability of a magnetic material to be measured or an amount correlated with the differential magnetic permeability is measured, a direct-current magnetic field is controlled to make the measurement value constant (magnetization up to a rotating magnetization region), and in this state, electromagnetic characteristics of the magnetic material to be measured are measured using an alternating-current magnetic field to measure the material characteristics (claim 1 in Patent Document 3).

In the detection of a poorly quenched portion generated in a part of a cross-section using the method described in Patent Document 3, the measurement is performed in the rotating magnetization region, that is, the near-saturation region in the magnetic characteristic curve. The near-saturation region is positioned in the first or third quadrant of the magnetic characteristic curve expressed in an orthogonal coordinate system.

However, as will be described later, it has been found that in a case where the inventors acquire a magnetic characteristic curve by inserting a pipe into an exciting coil and a detecting coil, the shape of the acquired magnetic characteristic curve in the near-saturation region is substantially the same regardless of the presence or absence of a poorly quenched portion generated in a part of a cross-section. Accordingly, with the method described in Patent Document 3, a poorly quenched portion generated in a part of a cross-section cannot be accurately detected.

In the above description, the description has been given using a pipe as an example, but the above-described problem is not limited to the case of the pipe. This problem is also common to other long materials such as a steel bar. In addition, in the above description, a heat treatment is used as an example of a cause of the material characteristic change, but a similar problem may be caused due to a cause other than the heat treatment, such as the magnitude of hardening accompanying the processing or a change in the carbon amount accompanying decarburizing or carburizing.

CITATION LIST

Patent Document

[Patent Document 1]
Japanese Unexamined Patent Application, First Publication No. 2002-14081
[Patent Document 2]
Japanese Unexamined Patent Application, First Publication No. 2001-133441
[Patent Document 3]
Japanese Unexamined Patent Application, First Publication No. 2005-257701

SUMMARY OF THE INVENTION

Problems to be Solved by the Invention

The invention is contrived in view of the above-described circumstances, and an object thereof is to provide a device and a method of detecting magnetic characteristic change for a long material, which can reduce a dead zone of an end portion of the long material in a longitudinal direction and can accurately detect portions where magnetic characteristics change over the whole length thereof.

Means for Solving the Problem

In order to solve the problem, the inventors have conducted intensive studies, and found that a slight significant difference is generated between the shapes of magnetic characteristic curves acquired by magnetizing a long material in a case where there is a portion where magnetic characteristics change (hereinafter, may be referred to as "abnormal portion") such as a poorly quenched portion in a part of a cross-section of the long material and in a case where there is no portion where magnetic characteristics change. Specific description thereof is as follows.

In the method described in Patent Document 2, as described above, a field intensity when the amplitude of the Barkhausen noise reaches the maximum is used as a magnetic measurement value having good correlation with the hardness of a material. Since the field intensity when the amplitude of the Barkhausen noise reaches the maximum is close to a value of a coercive force which is an intersection of a magnetic characteristic curve and a horizontal axis (field intensity), it can also be thought that the method described in Patent Document 2 uses a coercive force as a magnetic measurement value having good correlation with the hardness of a material. The method using a coercive force is effective for a case where a measurement target material is made of a substance which is regarded to be substantially the same. In addition, this method is not suitable for a measurement target in which there is only a small number of abnormal portions in a normal material. The coercive force is a field intensity when a magnetic flux density in a material is zero after the magnetization of the material in one direction and the application of a magnetic field in the reverse direction, and is a measurement value in a situation in which a relatively large magnetic field is applied such that magnetic domains in the material are randomly aligned. Accordingly, in both of a case where there is a magnetically soft material as an abnormal portion in a part of a magnetically hard material and an opposite case where there is a magnetically hard material as an abnormal portion in a part of a magnetically soft material, the coercive force is a measurement value in a situation in which the movement of magnetic domains of both the materials is started already. Therefore, with the method using a coercive force, only a small number of magnetically abnormal portions contained cannot be accurately detected.

In the course of from a state in which the material is strongly magnetized in one direction to a state in which the field intensity progressively increases in the reverse direction through a state in which the field intensity is zero, that is, in the second or fourth quadrant of a magnetic characteristic curve, the movement of magnetic domains of the magnetically soft material is started in a state in which magnetic domains of the magnetically hard material do not move, and in a case where the field intensity further increases thereafter, the movement of magnetic domains of the hard material is started. That is, in the second or fourth quadrant, even in a case where the abnormal portion is either the magnetically hard material or the magnetically soft material, both the materials have different magnetic domain movement start timings and are different in terms of the inclination of a tangent of the magnetic characteristic curve. Accordingly, it has been found that in a case where there is an abnormal portion in a part of a measurement target material, the shape of a magnetic characteristic curve is changed with respect to a normal material such that the inclination of a tangent of the magnetic characteristic curve has a local maximum or minimum value at a field intensity at which the superposition of the characteristics of the magnetically hard material and the magnetically soft material is started.

In order to solve the problem, the invention employs the followings.

(1) A device of detecting magnetic characteristic change for a long material according to an aspect of the invention which detects portions where magnetic characteristics change in the long material, including: an exciting coil into which the long material is inserted and which magnetizes the long material in a longitudinal direction; a detecting coil into which the long material is inserted and which detects a magnetic flux generated in the long material due to magnetization by the exciting coil; and a yoke member which has a first opening portion which is positioned on one side of the long material in the longitudinal direction and into which the long material is inserted and a second opening portion which is positioned on the other side of the long material in the longitudinal direction and into which the long material is inserted, and has a shape which is substantially axially symmetrical about an axis passing the first opening portion and the second opening portion, in which the exciting coil and the detecting coil are surrounded by the yoke member, the first opening portion, and the second opening portion.

Since the device of detecting magnetic characteristic change for a long material according to (1) employs an encircling coil type including the exciting coil and the detecting coil into which the long material is inserted, the long material can be directly magnetized and a temporal change of the magnetic flux in the long material can be directly detected by the detecting coil.

In addition, since the device of detecting magnetic characteristic change for a long material further includes the yoke member which surrounds the exciting coil and the detecting coil and has a substantially axially symmetrical shape, the magnetic flux generated in the long material due to magnetization by the exciting coil can be forcibly introduced to the yoke member in any portion in the longitudinal direction of the long material. That is, since the magnetic path of the magnetic flux generated in the long material is a closed magnetic path, the magnetization state of the long material is rarely influenced by the position of an end portion of the long material in the longitudinal direction, differing from a case where the magnetic path is an open magnetic path. That is, it is possible to obtain a constant magnetization state of the long material even in a case where the end portion of the long material in the longitudinal direction is sufficiently separated from an end portion of the exciting coil. Thus, a dead zone of the end portion of the long material in the longitudinal direction can be reduced. In addition, the magnetic flux generated in the long material becomes substantially uniform in any portion in the longitudinal direction of the long material. That is, since a magnetic circuit formed by the long material and the yoke member has axial symmetry, portions where magnetic characteristics change can be accurately detected over the whole length thereof even in a case where the portions where magnetic characteristics change exist in any portion in the longitudinal direction of the long material.

For example, in a case where portions where magnetic characteristics change are detected during the movement of the long material, it is possible to transmit without leakage of magnetic flux by virtue of the substantially axially symmetrical yoke member even in a case where the variation of pass-line of the long material occurs in any direction perpendicular to the longitudinal direction of the long material. That is, it is possible to reduce the influence of the variation of pass-line in a case where the long material is moved.

The device of detecting magnetic characteristic change for a long material according to the aspect according to (1) is particularly useful in a case where the exciting coil, the detecting coil, and the yoke member are fixed and the long material is relatively moved in the longitudinal direction of the long material, but is not limited to this configuration. That is, a form in which the exciting coil, the detecting coil, and the yoke member are moved in the longitudinal direction of the long material in a state in which the long material is stopped can also be employed. In addition, the detection may be performed in a fixed state in which all of the long material, the exciting coil, the detecting coil, and the yoke member are not moved.

(2) In the aspect according to (1), a minimum cross-sectional area of the yoke member may be equal to or greater than that of the long material when viewed from a cross-section perpendicular to a direction in which the magnetic flux flows.

According to the aspect according to (2), in a case where a cross-section of the opening portion of the yoke member has a larger amount of magnetic flux than those introduced to a cross-section of the long material from the cross-section of the opening portion of the yoke member, it is possible to introduce the magnetic flux to the cross-section of the long material without saturating the magnetic flux.

(3) In the aspect according to (1) or (2), the following configuration may be employed: a plurality of the detecting coils are provided; and at least one of the detecting coils is provided at at least one of the position of the first opening portion and the position of the second opening portion.

According to the aspect according to (3), it is possible to reduce a dead zone generated in at least one of a front end and a rear end of the long material.

(4) The device of detecting magnetic characteristic change for a long material according to any one of (1) to (3) may further include: a feeding mechanism which relatively moves the long material in the longitudinal direction with respect to the exciting coil, the detecting coil, and the yoke member.

According to the aspect according to (4), by the feeding mechanism, it is possible to detect portions where magnetic characteristics change while continuously conveying the long material. That is, it is possible to stably and continuously inspect the long material with a wide detection range while suppressing the variation of pass-line of the long material.

(5) The device of detecting magnetic characteristic change for a long material according to any one of (1) to (4) may further include: a detector which detects the portions where magnetic characteristics change based on an output voltage of the detecting coil, the detector may previously store, as a reference curve, a magnetic characteristic curve acquired based on an output voltage of the detecting coil in a case where a reference material which is a long material having predetermined hardness is magnetized by the exciting coil, and the detector may execute a procedure for acquiring a magnetic characteristic curve which is a test curve based on an output voltage of the detecting coil in a case where a test material which is a long test target material is magnetized by the exciting coil, a procedure for simultaneously displaying the reference curve and the test curve in the same orthogonal coordinate system, and a procedure for detecting the portions where magnetic characteristics change in the test material based on a difference in the shape between the reference curve and the test curve.

According to the aspect according to (5), since the detector executes the procedure for simultaneously displaying the reference curve and the test curve in the same orthogonal coordinate system, for example, a slight difference in the shape between the magnetic characteristic curves can be relatively easily recognized by visually observing the shapes of the reference curve and the test curve displayed, and in accordance with the magnitude of the difference in the shape, the portions where magnetic characteristics change in the test material can be accurately detected.

(6) In the aspect according to (5), the detector may detect the portions where magnetic characteristics change in the test material based on a difference between a change of an inclination of a tangent of the reference curve and a change of an inclination of a tangent of the test curve.

According to the aspect according to (6), a procedure for automatically detecting the portions where magnetic characteristics change in the test material accurately can be executed in accordance with the magnitude of the change of the inclination of the tangent of each magnetic characteristic curve at a field intensity within a predetermined range.

(7) In the aspect according to (6), the detector may detect the portions where magnetic characteristics change in the test material based on a difference between a time differential value of an output voltage of the detecting coil obtained regarding the reference material and a time differential value of an output voltage of the detecting coil obtained regarding the test material.

According to the aspect according to (7), the portions where magnetic characteristics change in the test material can be automatically detected accurately in accordance with, for example, the magnitude of a time differential value of the output voltage of the detecting coil obtained regarding each long material for a predetermined period of time.

According to the device of detecting magnetic characteristic change for a long material according to the invention, it is possible to accurately detect the portions where magnetic characteristics change in the test material by both the judgement by visual observation by an operator and the automatic detection by the detector.

(8) The device of detecting magnetic characteristic change for a long material according to any one of (5) to (7) may be positioned in a rear stage of quenching of the long material.

(9) A method of detecting magnetic characteristic change for a long material which detects portions where magnetic characteristics change in the long material using the device of detecting magnetic characteristic change for a long material according to any one of (1) to (8), including: a first step in which a long material having predetermined hardness is prepared as a reference material, a magnetic characteristic curve is acquired by magnetizing the reference material, and the acquired magnetic characteristic curve is defined as a reference curve; a second step in which a magnetic characteristic curve is acquired by magnetizing a test material which is a long test target material under the same conditions as in the first step, and the acquired magnetic characteristic curve is defined as a test curve; a third step in which the reference curve and the test curve are simultaneously displayed in the same orthogonal coordinate system; and a fourth step in which the portions where magnetic characteristics change in the test material are detected based on a difference in the shape between the reference curve and the test curve.

According to the aspect according to (9), by executing the first to third steps, the reference curve which is a magnetic characteristic curve of the reference material (normal long material having no abnormal portions) and the test curve which is a magnetic characteristic curve of the test material (long test target material), which have been acquired under the same magnetization conditions, are simultaneously displayed in the same orthogonal coordinate system (with a vertical axis indicating a magnetic flux density and a horizontal axis indicating an exciting current). Accordingly, for example, a slight difference in the shape between the magnetic characteristic curves can be relatively easily recognized by visually observing the shapes of the reference curve and the test curve displayed. That is, even in a case where a slight change in the shape (a change in the shape of the test curve from the reference curve) caused by the portions where magnetic characteristics change existing in the test material cannot be recognized only by displaying the test curve, the difference in the shape can be actualized by simultaneously displaying the reference curve and the test curve. The portions where magnetic characteristics change in the test material can be accurately detected in accordance with the magnitude of the difference in the shape.

In the invention, the fact that there is no portion where magnetic characteristics change (abnormal portion) in the reference material can be recognized by, for example, previously performing a hardness test. A reference material is preferably made of the same material and preferably has the same cross-sectional size as a test material. In a case where a plurality of test materials are tested, a common single reference material may be used as long as the test materials are made of the same material and have the same cross-sectional size. However, in a case where test materials which are made of different materials and have different cross-sectional sizes are tested, a new reference material according thereto is preferably used.

In the invention, the "magnetize . . . under the same conditions" means that the magnetization is performed with the same frequency and amplitude of the exciting current using the same magnetization unit (magnetization coil or the like).

(10) In the aspect according to (9), in the fourth step, the portions where magnetic characteristics change in the test material may be detected based on a difference between a change of an inclination of a tangent of the reference curve and a change of an inclination of a tangent of the test curve.

According to the results of the intensive studies of the inventors, it has been found that in the fourth step of the invention, the difference in the shape between the reference curve and the test curve which is used to detect the portions where magnetic characteristics change in the test material is actualized by a difference between a change of the inclination of the tangent of the reference curve (corresponding to a change of the differential magnetic permeability) and a change of the inclination of the tangent of the test curve (corresponding to a change of the differential magnetic permeability). That is, according to the aspect according to (10), the portions where magnetic characteristics change in the test material can be accurately detected.

In the above-described preferable method, for example, the change of the inclination of the tangent of the reference curve and the change of the inclination of the tangent of the test curve may be simultaneously displayed in the same orthogonal coordinate system with a vertical axis indicating a magnitude of the change and a horizontal axis indicating an exciting current, and the portions where magnetic characteristics change in the test material may be detected by visually observing the display. Otherwise, for example, it is also possible to employ a method of automatically detecting the portions where magnetic characteristics change in the test material in accordance with the magnitude of the change of the inclination of the tangent of each magnetic characteristic curve at a field intensity within a predetermined range.

(11) In the aspect according to (10), in the first step, the reference material may be inserted into the exciting coil and the detecting coil to magnetize the reference material by the exciting coil in a longitudinal direction, and a magnetic flux generated in the reference material due to magnetization by the exciting coil may be detected by the detecting coil to acquire the reference curve, in the second step, the test material may be inserted into the exciting coil and the detecting coil to magnetize the test material by the exciting coil in a longitudinal direction, and a magnetic flux generated in the test material due to magnetization by the exciting coil may be detected by the detecting coil to acquire the test curve, and in the fourth step, the portions where magnetic characteristics change in the test material may be detected based on a difference between a time differential value of an output voltage of the detecting coil obtained regarding the reference material and a time differential value of an output voltage of the detecting coil obtained regarding the test material.

According to the aspect according to (11), in the detecting coil, an induced electromotive force according to a temporal change of the magnetic flux generated in the reference material is generated, and an output voltage according to the induced electromotive force is output from the detecting coil. By time-integrating the output voltage of the detecting coil, the magnitude and the density of the magnetic flux generated in the reference material can be measured. This is also similar to the acquisition of the test curve.

Here, in order to acquire a magnetic characteristic curve such as the reference curve and the test curve, a triangular or sinusoidal wave exciting current is applied to the exciting coil. However, in this case, the inclination (differential magnetic permeability) of a tangent of the magnetic characteristic curve is correlated with the output voltage of the detecting coil (in a case where the exciting current is a triangular wave, the differential magnetic permeability is proportional to the output voltage of the detecting coil). Accordingly, a change of the inclination of the tangent of the magnetic characteristic curve can be recognized by time-differentiating the output voltage of the detecting coil. In other words, the portions where magnetic characteristics change in the test material can be detected by calculating a time differential value of the output voltage of the detecting coil, instead of directly calculating a change of the inclination of the tangent of the magnetic characteristic curve.

In the above-described preferable method, for example, the time differential value of the output voltage of the detecting coil obtained regarding the reference material and the time differential value of the output voltage of the detecting coil obtained regarding the test material may be simultaneously displayed in the same orthogonal coordinate system with a vertical axis indicating a time differential value of the output voltage of the detecting coil and a horizontal axis indicating a time, and the portions where magnetic characteristics change in the test material may be detected by visually observing the display. Otherwise, for example, it is also possible to employ a method of automatically detecting the portions where magnetic characteristics change in the test material in accordance with the magnitude of a time differential value of the output voltage of the detecting coil obtained regarding each long material (reference material and test material) for a predetermined period of time.

Effects of the Invention

According to the aspects of the invention, it is possible to reduce a dead zone of an end portion of a long material in a longitudinal direction and to accurately detect portions where magnetic characteristics change over the whole length thereof.

DETAILED DESCRIPTION OF THE INVENTION

Hereinafter, a device of detecting magnetic characteristic change for a long material (hereinafter, appropriately simply referred to as "device of detecting magnetic characteristic change") according to an embodiment of the invention will be described with appropriate reference to the accompanying drawings. In this embodiment, the description will be given using a case in which the long material is a pipe and the pipe is conveyed in a longitudinal direction thereof as an example. In this specification and the drawings, elements having substantially the same function and configuration will be denoted by the same references and overlapping description will be omitted.

Figure 1A:
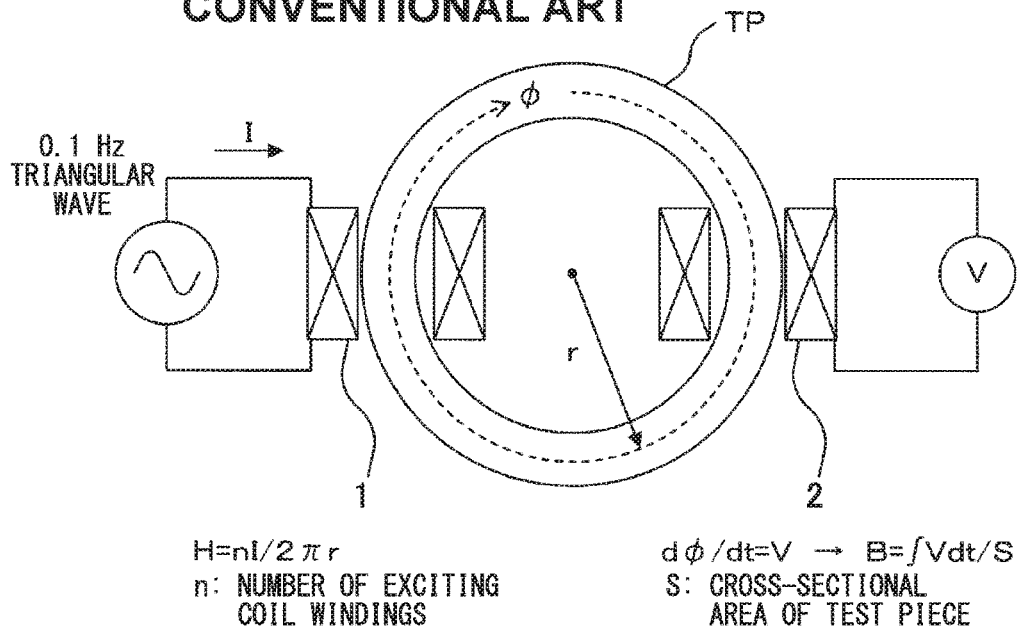
FIG. 1A is a diagram for showing a conventional method of measuring magnetic characteristics of a pipe, and is a diagram briefly showing the measurement method using a test piece.
Figure 1B:
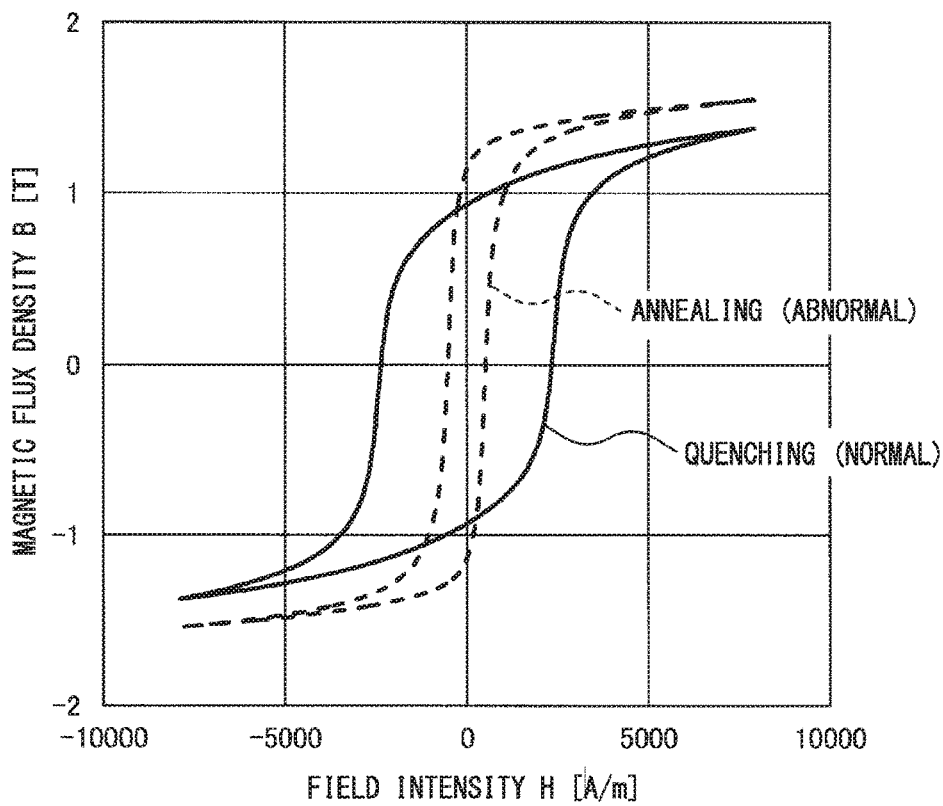
FIG. 1B is a graph showing an example of measurement results obtained by the measurement method shown in FIG. 1A.
Figure 2A:
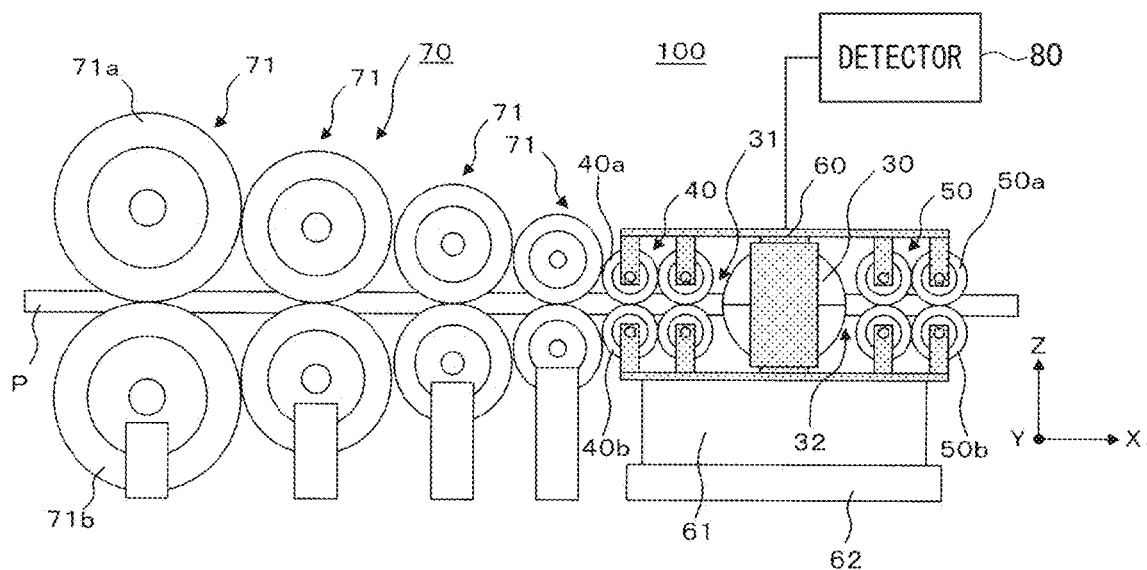
FIG. 2A is a side view schematically showing a configuration of a device of detecting magnetic characteristic change according to an embodiment of the invention.
Figure 2B:
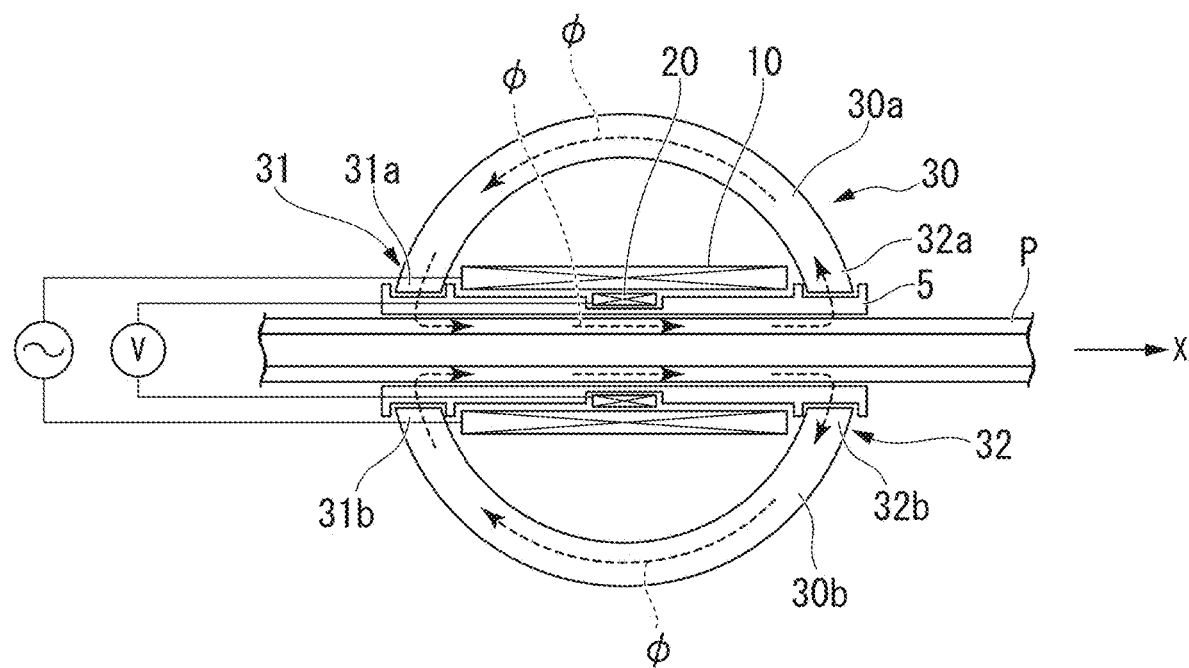
FIG. 2B is a view schematically showing a configuration of an exciting coil, a detecting coil, a bobbin, and a yoke member of the device of detecting magnetic characteristic change according to the embodiment, and is a cross-sectional view when the configuration is viewed from a longitudinal section including a central axis of a pipe.
Figure 2C:
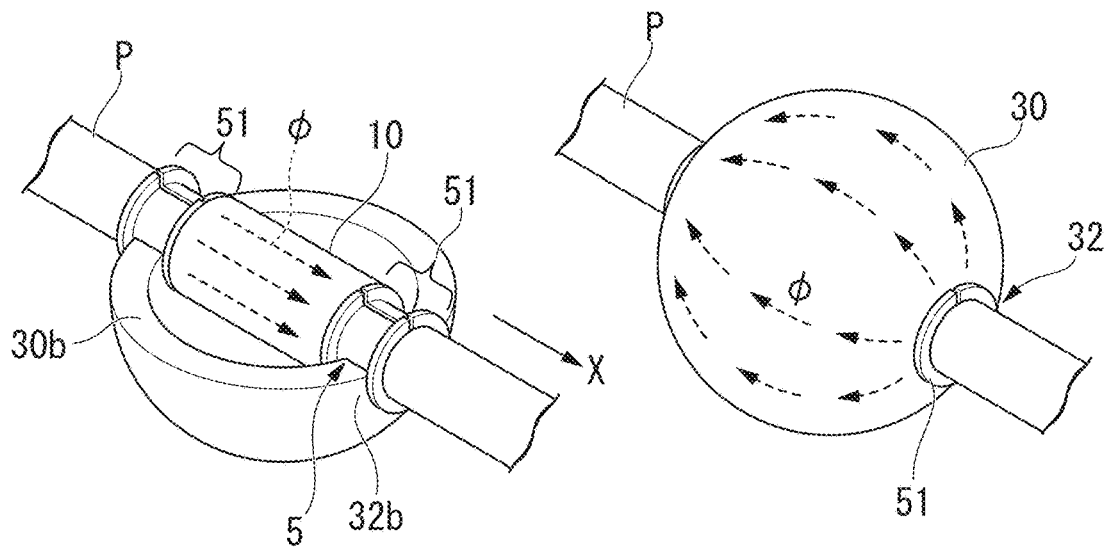
FIG. 2C is a perspective view schematically showing a configuration of the exciting coil, the bobbin, and the yoke member of the device of detecting magnetic characteristic change according to the embodiment.

FIG. 2A is a side view schematically showing a configuration of a device of detecting magnetic characteristic change 100 according to an embodiment of the invention, FIG. 2B is a cross-sectional view schematically showing a configuration of an exciting coil 10, a detecting coil 20, a bobbin 5, and a yoke member 30 according to the embodiment, and FIG. 2C is a perspective view schematically showing a configuration of the exciting coil 10, the bobbin 5, and the yoke member 30 according to the embodiment. In FIG. 2C, the left view shows a state in which one member piece 30b constituting the yoke member 30 is removed, and the right view shows a state in which the member piece is not removed.

As shown in FIG. 2A, the device of detecting magnetic characteristic change 100 according to this embodiment is a device which detects portions where magnetic characteristics change associated with a change in the magnetic characteristics of a pipe P which is conveyed in a longitudinal direction (X-direction shown in FIG. 2A). Specifically, the device of detecting magnetic characteristic change 100 is a device which detects portions where magnetic characteristics change of the material characteristics by a heat treatment. The device of detecting magnetic characteristic change 100 according to this embodiment is positioned, for example, in a rear stage of quenching of a long material.

As shown in FIGS. 2A and 2B, the device of detecting magnetic characteristic change 100 according to this embodiment is mainly provided with the exciting coil 10, the detecting coil 20, the yoke member 30, the bobbin 5, and a detector 80. As a preferable configuration, the device of detecting magnetic characteristic change 100 according to this embodiment is further provided with a first pair of restriction rollers 40, a second pair of restriction rollers 50, a holding member 60, and a guide roller group 70.

As shown in FIGS. 2B and 2C, the exciting coil 10 is a coil into which a pipe P is inserted and which magnetizes the pipe P in a longitudinal direction (X-direction). Specifically, the exciting coil 10 according to this embodiment is wound around an outer surface of the hollow bobbin 5 through which the pipe P passes. For example, a low-frequency AC current is applied to the exciting coil 10 and the pipe P is magnetized in the X-direction, so that a magnetic flux $\phi$ is generated. In FIGS. 2B and 2C, the magnetic flux $\phi$ is shown by the broken line. The magnetic flux $\phi$ shown in the left view in FIG. 2C is a magnetic flux which is generated in the exciting coil 10.

As shown in FIG. 2B, the detecting coil 20 is a coil into which the pipe P is inserted and which detects a magnetic flux $\phi$ generated in the pipe P due to magnetization by the exciting coil 10. Specifically, similarly to the exciting coil 10, the detecting coil 20 according to this embodiment is wound around the outer surface of the bobbin 5. However, the detecting coil 20 is wound on the inside of the exciting coil 10 at a central position of the outer surface of the bobbin 5 in the X-direction. In the detecting coil 20, an induced electromotive force according to a temporal change of the magnetic flux $\phi$ generated in the pipe P is generated, and an output voltage according to the induced electromotive force is output from the detecting coil 20 to the detector 80. By measuring the induced electromotive force, a magnitude of the magnetic flux $\phi$ and a density of the magnetic flux generated in the pipe P can be measured.

In order to uniformly magnetize the pipe P, the exciting coil 10 is preferably long between a first opening portion 31 and a second opening portion 32. In HG 2B, the long material is inserted into one detecting coil 20 at the central position of the exciting coil 10. However, a plurality of detecting coils 20 may be provided and at least one of the detecting coils 20 may be provided at at least one of the position of the first opening portion 31 and the position of the second opening portion 32 to reduce a dead zone generated in at least one of a front end and a rear end of the pipe P.

The detector 80 detects portions where magnetic characteristics change based on the output voltage of the detecting coil 20. The detector 80 is provided with, for example, an A/D converter which A/D-converts the output voltage of the detecting coil 20 and a general-purpose personal computer in which a program for executing a predetermined procedure for detecting portions where magnetic characteristics change based on the output voltage of the detecting coil 20 A/D-converted by the A/D converter is installed. Details of the predetermined procedure which is executed by the detector 80 will be described later.

As shown in FIG. 2B, the yoke member 30 has: the first opening portion 31 which is positioned on the upstream side in the conveyance direction (X-direction) of the pipe P and into which the pipe P is inserted; and the second opening portion 32 which is positioned on the downstream side in the conveyance direction of the pipe P and into which the pipe P is inserted. The first opening portion 31 and the second opening portion 32 according to this embodiment have a substantially circular shape when viewed from the X-direction. The yoke member 30 has a shape which is substantially axially symmetrical about the axis (central axis in the X-direction) passing the first opening portion 31 and the second opening portion 32. The exciting coil 10 and the detecting coil 20 are surrounded by the yoke member 30, the first opening portion 31, and the second opening portion 32.

As shown in FIGS. 2B and 2C, the yoke member 30 has a spherical shape, and includes member pieces 30a and 30b, each having a semi-spherical shape. Specifically, portions (portions having a semi-circular shape when viewed from the X-direction) 31a and 32a forming the first opening portion 31 and the second opening portion 32 of the member piece 30a, respectively, and portions (portions having a semi-circular shape when viewed from the X-direction) 31b and 32b forming the first opening portion 31 and the second opening portion 32 of the member piece 30b, respectively, are fitted to grooves of flange portions 51 formed in end portions of the bobbin 5, respectively, and thus the member pieces 30a and 30b are formed integrally with each other, and the yoke member 30 having a spherical shape is formed. The end portions of the member pieces 30a and 30b on the upstream side in the conveyance direction (X-direction) of the pipe P, that is, the portions 31a and 31b of the member pieces 30a and 30b which form the first opening portion 31 are positioned on the upstream side of the end portions of the exciting coil 10 and the detecting coil 20 on the upstream side in the conveyance direction (X-direction) of the pipe P. In addition, the end portions of the member pieces 30a and 30b on the downstream side in the conveyance direction (X-direction) of the pipe P, that is, the portions 32a and 32b of the member pieces 30a and 30b which form the second opening portion 32 are positioned on the downstream side of the end portions of the exciting coil 10 and the detecting coil 20 on the downstream side in the conveyance direction (X-direction) of the pipe P. Furthermore, the first opening portion 31 and the second opening portion 32 are closer to the pipe P than a portion near the center of the yoke member 30. Accordingly, the exciting coil 10 and the detecting coil 20 are surrounded by the yoke member 30, the first opening portion 31, and the second opening portion 32.

The yoke member 30 according to this embodiment has a spherical shape, but in the invention, the shape of the yoke member is not limited to the spherical shape. Various configurations can be employed in a case where the yoke member has a substantially axially symmetrical shape such as a spheroidal shape or a cylindrical shape. Another embodiment of the yoke member 30 will be described later. The yoke member 30 according to this embodiment has no opening portion, except for the first opening portion 31 and the second opening portion 32. However, in a case where the yoke member 30 is not strictly required to be axially symmetrical since the change in the magnetic characteristics is large, for example, a slit portion extending along the central axis may be formed in a part of the yoke member 30 to reduce the weight of the yoke member 30.

As described above, the device of detecting magnetic characteristic change 100 according to this embodiment is provided with the exciting coil 10 and the detecting coil 20 into which a pipe P is inserted. That is, since the exciting coil 10 and the detecting coil 20 provided are encircling coil types, the pipe P can be directly magnetized and a temporal change of the magnetic flux in the pipe P can be directly detected by the detecting coil 20.

In addition, since the device of detecting magnetic characteristic change 100 according to this embodiment is provided with the yoke member 30 which has a substantially axially symmetrical shape, and the exciting coil 10 and the detecting coil 20 are surrounded by the yoke member 30, the first opening portion 31, and the second opening portion 32, the magnetic flux φ (see FIGS. 2B and 2C) generated in the pipe P due to magnetization by the exciting coil 10 can be forcibly introduced to the yoke member 30 in any portion in the longitudinal direction of the pipe P. That is, since the magnetic path of the magnetic flux φ generated in the pipe P is a closed magnetic path, the magnetization state of the pipe P is rarely influenced by the position of the end portion of the pipe P, differing from a case where the magnetic path is an open magnetic path. Thus, the dead zone of the end portion of the pipe can be reduced. In addition, since the magnetic flux φ generated in the pipe P becomes substantially uniform in any portion in the longitudinal direction of the pipe P, portions where magnetic characteristics change can be accurately detected over the whole length thereof even in a case where the portions where magnetic characteristics change exist in any portion in the longitudinal direction of the pipe P. In addition, in a case where a cross-section of the opening portion of the yoke member 30 has a larger amount of magnetic flux than those introduced to a cross-section of the pipe P from the cross-section of the opening portion of the yoke member, it is possible to introduce the magnetic flux to the cross-section of the pipe P without saturating the magnetic flux. Accordingly, the cross-sectional area of the yoke member 30 may be the same as that of the pipe P, and is preferably larger than that of the pipe P when viewed from a cross-section perpendicular to the direction in which the magnetic flux flows.

Figure 3A:
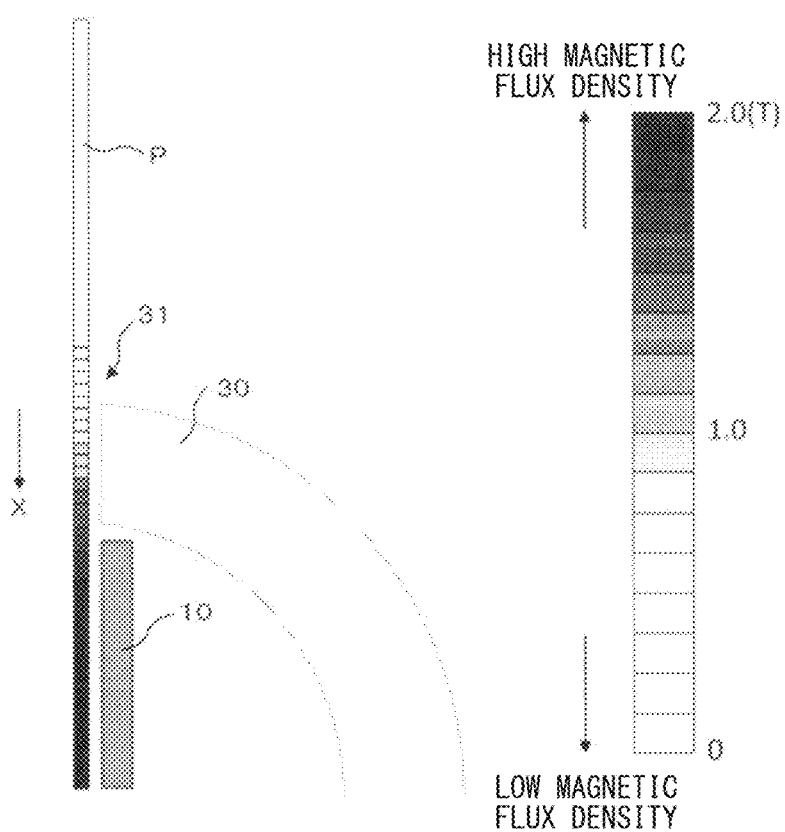
FIG. 3A is a diagram showing an example of results of an electromagnetic field analysis in a case where the yoke member is disposed.
Figure 3B:
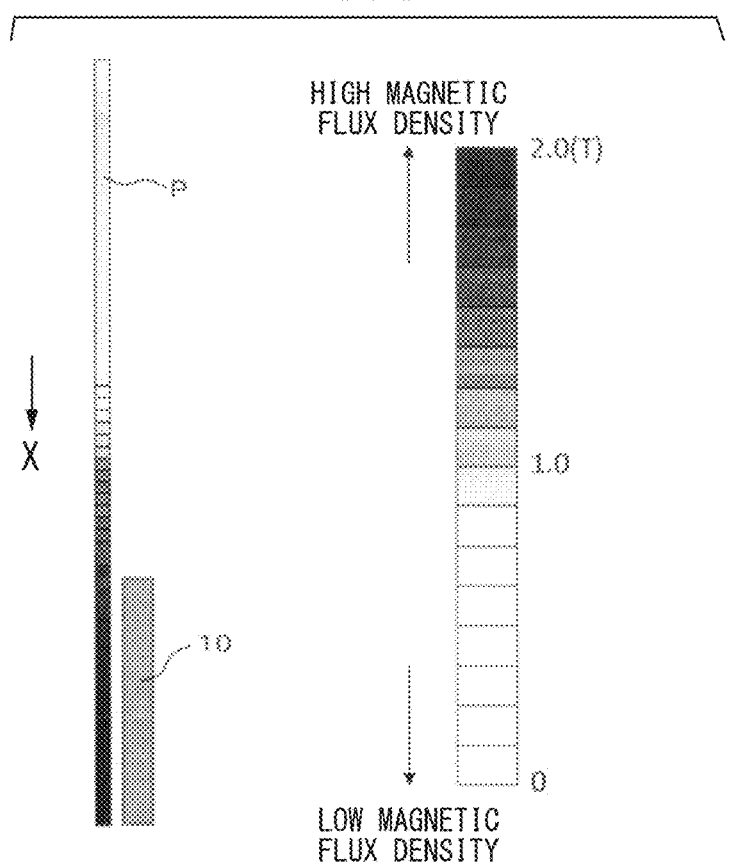
FIG. 3B is a diagram showing an example of results of an electromagnetic field analysis in a case where the yoke member is not disposed.

FIGS. 3A and 3B show an example of results of an electromagnetic field analysis for examining the influence of the presence of the yoke member 30 on the magnetization state of the pipe P. FIG. 3A shows analysis results in a case where the yoke member 30 is disposed, and FIG. 3B shows analysis results in a case where the yoke member 30 is not disposed. The left view in FIG. 3A and the left view in FIG. 3B are ¼ cross-sectional views of the pipe P and the exciting coil 10 in the X-direction. The left view in FIG. 3A shows a ¼ cross-sectional view of the yoke member 30 in the X-direction.

As shown in FIG. 3A, in a case where the yoke member 30 is disposed, little magnetic flux is generated in a portion of the pipe P positioned on the upstream side of the first opening portion 31 of the yoke member 30 in the conveyance direction (X-direction) of the pipe P. The same phenomenon is observed in a portion of the pipe P positioned on the downstream side of the second opening portion 32 of the yoke member 30 in the conveyance direction (X-direction) of the pipe P, although not shown in the drawing. In other words, the results shown in FIG. 3A show that even in a case where the end portion of the pipe P is positioned in any portion outside the yoke member 30, there is no influence on the magnetic flux generated in the portion of the pipe P in the yoke member 30.

In contrast, in a case where the yoke member 30 is not disposed as shown in FIG. 3B, a magnetic flux is generated in a portion of the pipe P positioned on the upstream side of the first opening portion 31 of the yoke member 30 in the conveyance direction (X-direction) of the pipe P in a case where the yoke member 30 is assumed to be disposed. The same phenomenon is observed in a portion of the pipe P positioned on the downstream side of the second opening portion 32 of the yoke member 30 in the conveyance direction (X-direction) of the pipe P, although not shown in the drawing, and the magnetic flux is widely distributed. In other words, the results shown in FIG. 3B show that the end portion of the pipe P has an influence on the magnetic flux generated in the portion of the pipe P positioned in the yoke member 30 according to the position of outside the yoke member 30 in a case where the yoke member 30 is assumed to be disposed.

Figure 4:
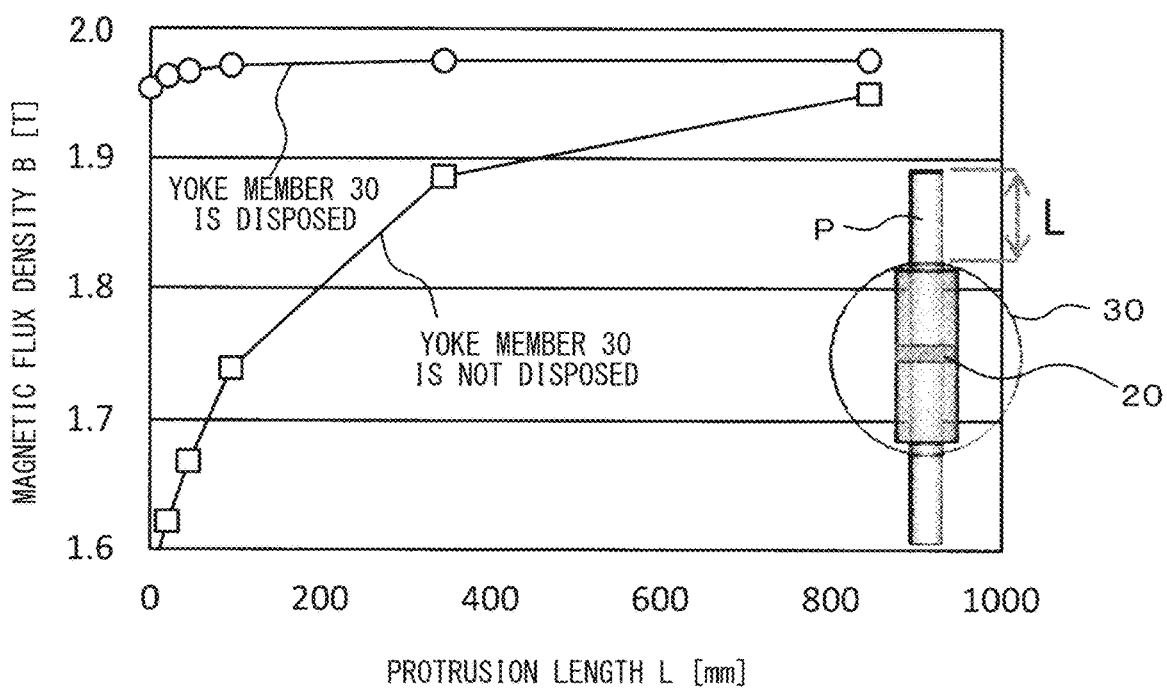
FIG. 4 is a graph showing an example of results obtained by calculating the relationship between a protrusion length of a portion of a pipe P positioned outside the yoke member and a magnetic flux density of the magnetic flux generated in a portion of the pipe at a position corresponding to a central position of the detecting coil by an electromagnetic field analysis.

FIG. 4 shows an example of results obtained by calculating the relationship between a protrusion length L (mm) of a portion of the pipe P positioned outside the yoke member 30 and a magnetic flux density B of the magnetic flux generated in a portion of the pipe P at a position corresponding to the central position of the detecting coil 20 by an electromagnetic field analysis. The results in a case where the yoke member 30 is not disposed are obtained by evaluating the protrusion length L with reference to the position of the yoke member 30 in a case where the yoke member 30 is assumed to be disposed. Specifically, the results shown in FIG. 4 are results of the electromagnetic field analysis based on the fact that a separation distance between the end portion of the pipe P on the upstream side in the conveyance direction in the exciting coil 10 and the inside of the first opening portion 31 of the yoke member 30 (and a separation distance between the end portion of the pipe P on the downstream side in the conveyance direction in the exciting coil 10 and the inside of the second opening portion 32 of the yoke member 30) is 5 mm, and the thickness of the yoke member 30 (a separation distance between the inside and the outside of the first opening portion 31 and a separation distance between the inside and the outside of the second opening portion 32) is 20 mm in a case where the yoke member 30 is disposed. Accordingly, in a case where the protrusion length is L (mm), the end portion of the pipe P protrudes from the end portion of the exciting coil 10 by L+25 mm with reference to the end portion of the exciting coil 10 in both of the case in which the yoke member 30 is disposed and the case in which the yoke member 30 is not disposed.

As shown in FIG. 4, in a case where the yoke member 30 is disposed, the magnetization state in the pipe P is found to be stabilized with a protrusion length of just 10 mm, as compared to a case where the yoke member 30 is not disposed.

From the results shown in FIGS. 3A, 3B, and 4, it is found that it is possible to reduce a dead zone of the end portion of the pipe P as described above according to the device of detecting magnetic characteristic change 100 according to this embodiment.

Figure 5A:
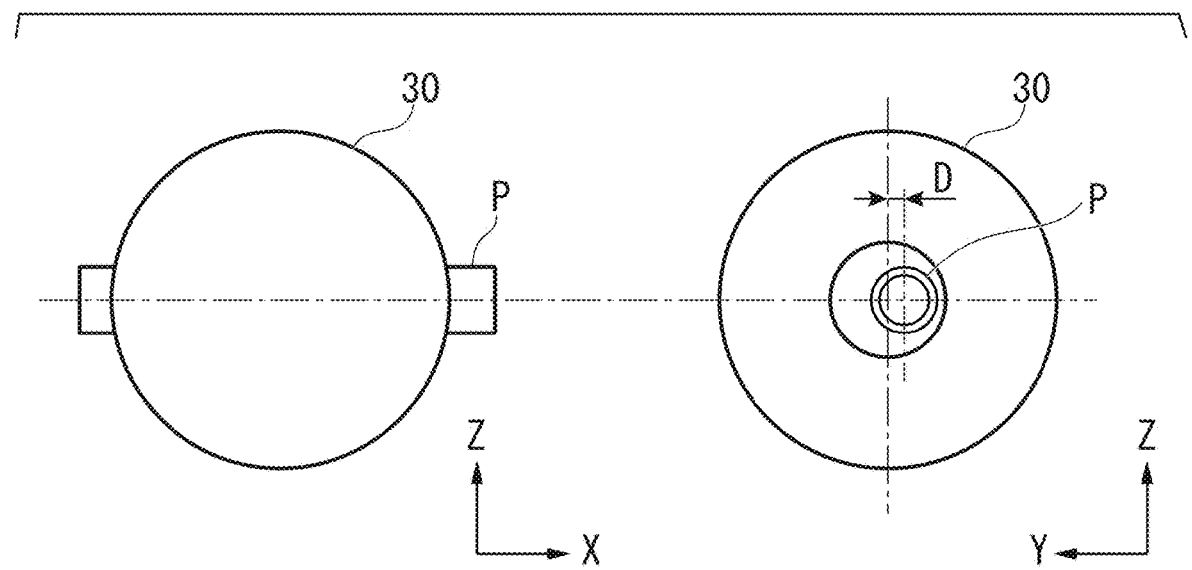
FIG. 5A is a diagram showing the variation of pass-line according to the embodiment.
Figure 5B:
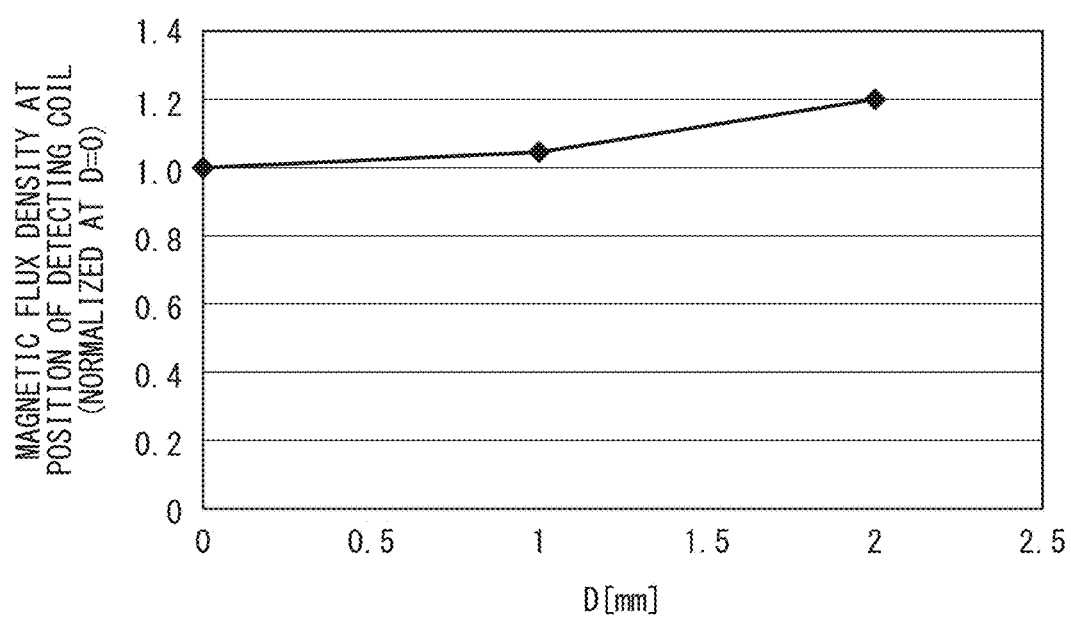
FIG. 5B shows an example of analysis results showing a change in the magnetic flux density of a long material at a position of the detecting coil in a case where the variation of pass-line of FIG. 5A occurs.
Figure 6A:
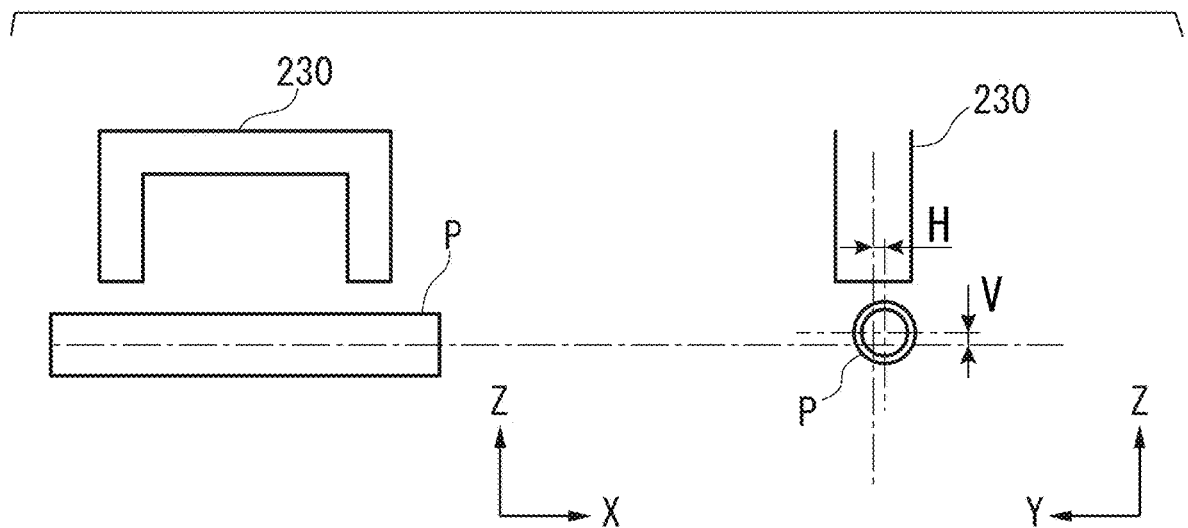
FIG. 6A is a diagram showing the variation of pass-line according to a conventional embodiment.
Figure 6B:
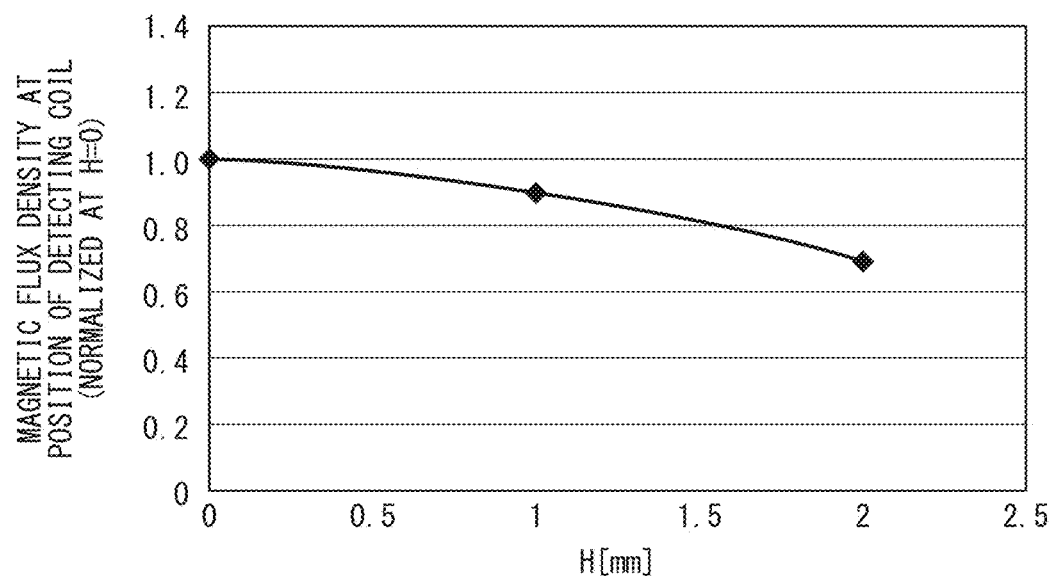
FIG. 6B shows an example of analysis results showing a change in the magnetic flux density of a long material at a position of the detecting coil in a case where the variation of pass-line occurs in a Y-axis direction in FIG. 6A.
Figure 6C:
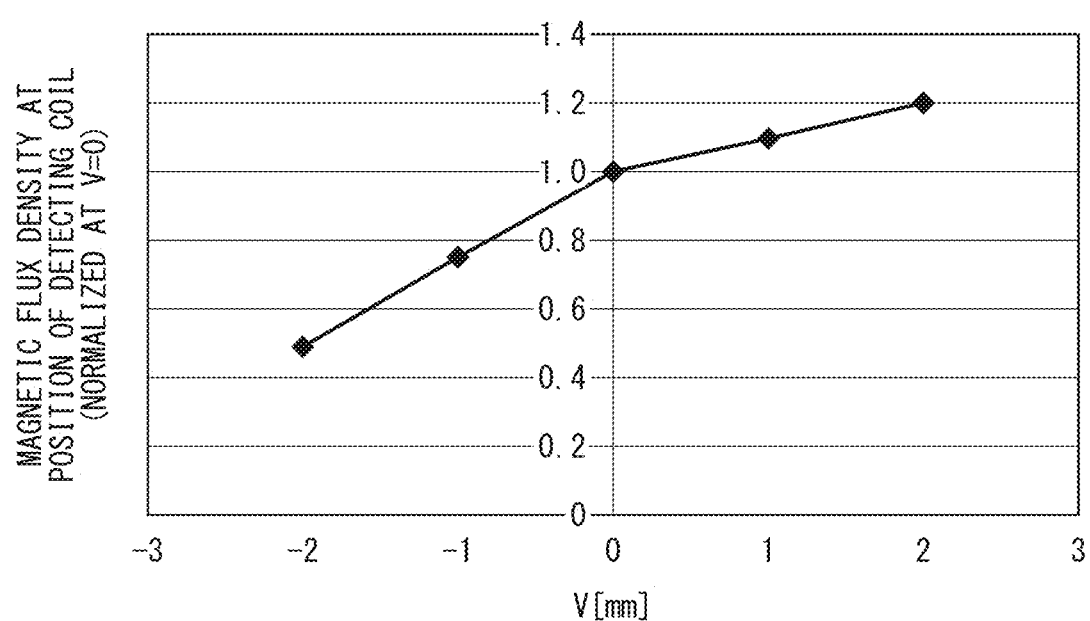
FIG. 6C shows an example of analysis results showing a change in the magnetic flux density of a long material at a position of the detecting coil in a case where the variation of pass-line occurs in a Z-axis direction in FIG. 6A.

In addition, in a case where the device of detecting magnetic characteristic change 100 according to this embodiment detects portions where magnetic characteristics change while moving the pipe P, the device of detecting magnetic characteristic change can transmit without leakage of magnetic flux by virtue of the substantially axially symmetrical yoke member 30 even in a case where the variation of pass-line occurs in a direction perpendicular to the longitudinal direction of the pipe P. FIGS. 5B, 6B, and 6C show an example of the results of an analysis of a change in the magnetic flux density for examining the influence of the variation of pass-line.

FIG. 5B shows analysis results showing a change in the magnetic flux density of a long material at a position of the detecting coil in a case where the variation of pass-line according to this embodiment occurs. As shown in HG 5B, when a pipe P is positioned at the center of the opening portion of the yoke member 30 (D=0 mm), the magnetic flux density of the pipe P is the minimum. The closer the pipe P is to the end portion of the opening portion of the yoke member 30 when viewed from the longitudinal direction of the pipe P, the higher the magnetic flux density of the pipe. Since the yoke member 30 has a substantially axially symmetrical shape, the magnetic flux density is not influenced by the direction of the variation of pass-line of the pipe P.

FIGS. 6B and 6C show analysis results showing a change in the magnetic flux density of a long material at a position of the detecting coil in a case where the variation of pass-line according to a conventional embodiment occurs. A yoke member 230 in FIG. 6A has a U-shape. As shown in FIG. 6B, the magnetic flux density of a pipe P according to a conventional embodiment is more largely influenced by the variation of pass-line than in the embodiment of the invention. As shown in FIGS. 6B and 6C, the way the magnetic flux density changes varies according to whether the pass-line of a pipe P moves in the Y-axis direction or the Z-axis direction. That is, in a case where the pass-line of the pipe moves obliquely to the Y-axis direction or the Z-axis direction, the change in the magnetic flux density is compositely influenced in the Y-axis direction and the Z-axis direction. Particularly, the magnetization force is significantly reduced when the pipe P is moved opposite to the yoke member 230 (minus direction of the Z-axis in FIG. 6A).

From the results shown in FIGS. 5B, 6B, and 6C, it is found that according to the device of detecting magnetic characteristic change 100 according to this embodiment, the influence of the variation of pass-line of a long material can be reduced in a case where the long material is relatively moved in a longitudinal direction thereof, as compared to a conventional embodiment.

The analysis according to this embodiment shown in HG 5B and the analysis according to the conventional embodiment shown in FIGS. 6B and 6C show results of the magnetic flux density analysis when magnetization is caused with the same magnetization force, that is, with the same number of coil windings and the same current value to assume that there is a variation of pass-line by a certain distance (for example, 2.0 mm) in the Y-axis direction and the Z-axis direction and the minimum distance between the magnetic pole (yoke member) and the pipe is set (for example, 2.0 mm).

In this embodiment, since the detecting coil is surrounded by the spherical yoke member 30, there is an effect that the detecting coil is shielded from electromagnetic noise of the surrounding environment. In addition, in a case where a ferromagnetic body is present nearby, the ferromagnetic body and the pipe form a magnetic circuit and the detecting coil detects the influence of the magnetic circuit in a conventional case. However, this embodiment has an advantage in that there is little influence of the surroundings since the detecting coil is shielded by the spherical yoke member 30.

A feeding mechanism according to an embodiment of the invention will be described.

The device of detecting magnetic characteristic change according to the embodiment is provided with a feeding mechanism which relatively moves a long material in a longitudinal direction with respect to the exciting coil, the detecting coil, and the yoke member.

As a preferable configuration of the feeding mechanism, the device of detecting magnetic characteristic change 100 according to this embodiment is provided with a first pair of restriction rollers 40, a second pair of restriction rollers 50, and a holding member 60 as shown in FIG. 2A. In addition, as a more preferable configuration, the device of detecting magnetic characteristic change 100 according to this embodiment is provided with a guide roller group 70.

Figure 7A:
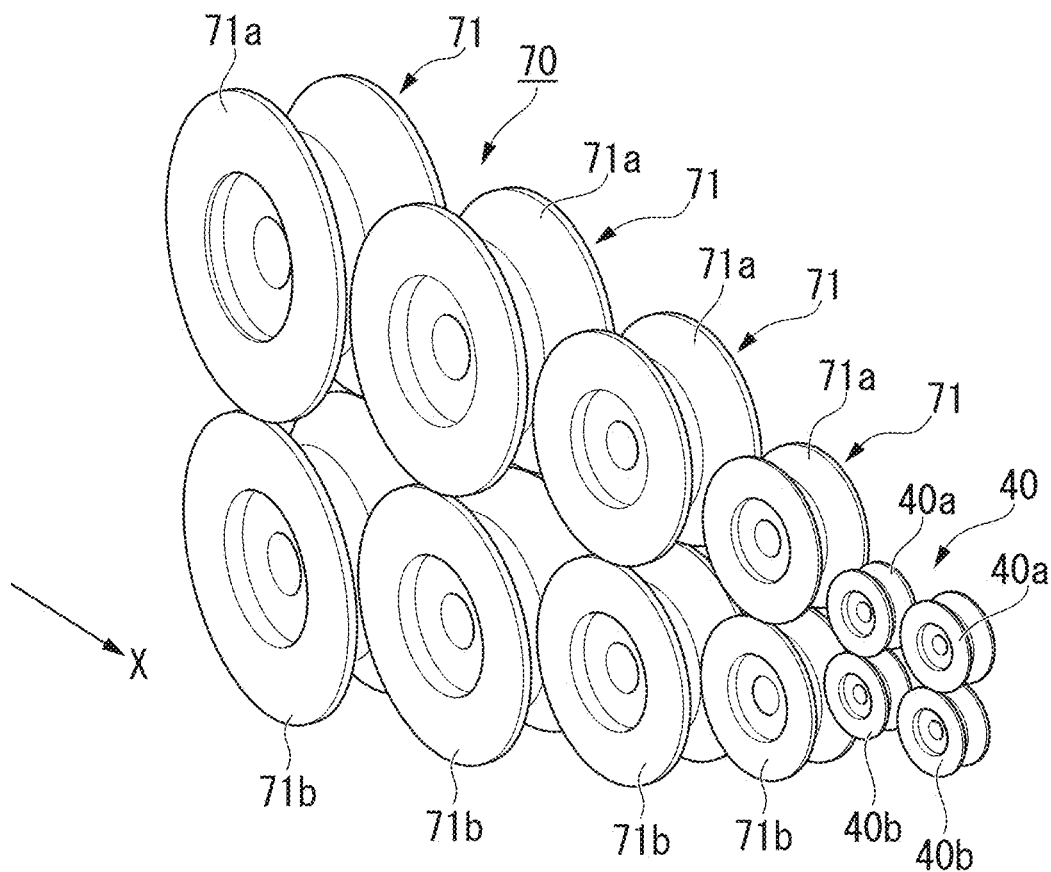
FIG. 7A is a perspective view showing a preferable configuration of a feeding mechanism according to the embodiment.
Figure 7B:
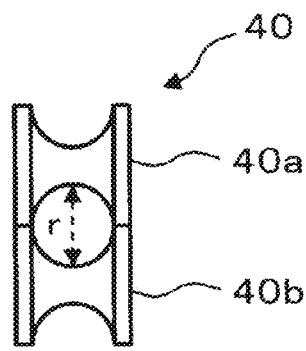
FIG. 7B is a front view of a first pair of restriction rollers shown in FIG. 7A.
Figure 7C:
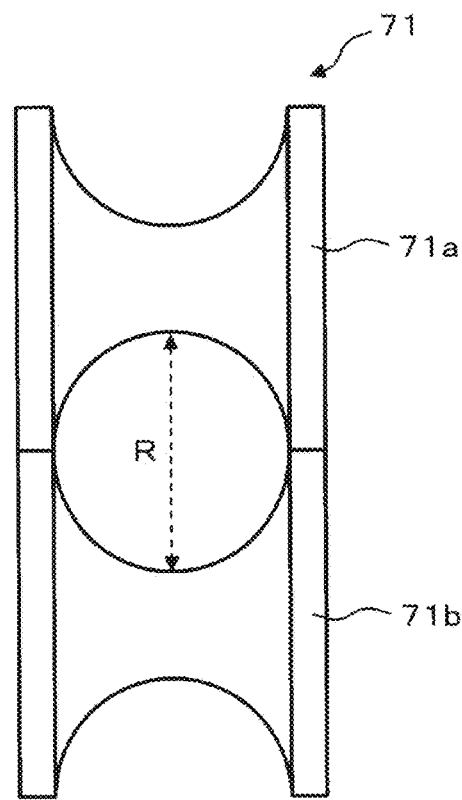
FIG. 7C is a front view of a guide roller group shown in FIG. 7A.

FIG. 7A is a perspective view showing a preferable configuration of the feeding mechanism according to the embodiment, and schematically shows a configuration of the first pair of restriction rollers 40 and the guide roller group 70. FIG. 7B shows the first pair of restriction rollers 40 viewed from the downstream side in a pipe conveyance direction (X-direction) according to the embodiment, and FIG. 7C shows a pair of guide rollers 71 constituting the guide roller group 70 viewed from the upstream side in the pipe conveyance direction (X-direction) according to the embodiment.

Hereinafter, the first pair of restriction rollers 40, the second pair of restriction rollers 50, the holding member 60, and the guide roller group 70 which constitute a preferable configuration of the feeding mechanism according to the embodiment will be sequentially described with appropriate reference to FIGS. 2A and 7A to 7C.

The first pair of restriction rollers 40 are positioned on the upstream side in a conveyance direction (X-direction) of a pipe P with respect to the first opening portion 31 of the yoke member 30 and are disposed to face each other with a gap interposed therebetween. In the examples shown in FIGS. 2A and 7A, first restriction rollers 40a and 40b constituting the first pair of restriction rollers 40 are disposed to face each other in a vertical direction. However, the invention is not limited to this form, and the rollers may be disposed to face each other in another direction such as a horizontal direction. In addition, as shown in FIG. 7B, each of the first restriction rollers 40a and 40b constituting the first pair of restriction rollers 40 according to this embodiment is a grooved roller, and a substantially circular groove which is formed by the first restriction rollers 40a and 40b corresponds to the above-described gap. The first pair of restriction rollers 40 function to guide a pipe P passing through the gap (groove) to the first opening portion 31 of the yoke member 30. As a preferable configuration, the size (diameter r of the groove) of the gap of the first pair of restriction rollers 40 according to this embodiment is substantially the same as the outer diameter of the pipe P. In addition, as a preferable configuration, two or more first pairs of restriction rollers 40 according to this embodiment (two pairs in the examples shown in FIGS. 2A and 7A) are disposed in the conveyance direction (X-direction) of the pipe P.

The second pair of restriction rollers 50 are positioned on the downstream side in a conveyance direction (X-direction) of a pipe P with respect to the second opening portion 32 of the yoke member 30 and are disposed to face each other with a gap interposed therebetween. In the examples shown in FIG. 2A, second restriction rollers 50a and 50b constituting the second pair of restriction rollers 50 are disposed to face each other in a vertical direction as in the case of the first pair of restriction rollers 40. However, the invention is not limited thereto, and the rollers may be disposed to face each other in another direction such as a horizontal direction. In addition, although omitted in the drawing, each of the second restriction rollers 50a and 50b constituting the second pair of restriction rollers 50 according to this embodiment is a grooved roller as in the case of the first restriction rollers 40a and 40b, and a substantially circular groove which is formed by the second restriction rollers 50a and 50b corresponds to the above-described gap. The second pair of restriction rollers 50 function to guide a pipe P inserted into the second opening portion 32 of the yoke member 30 and passing through the gap (groove). As a preferable configuration, the size (diameter of the groove) of the gap of the second pair of restriction rollers 50 according to this embodiment is substantially the same as the outer diameter of the pipe P. In addition, as a preferable configuration, two or more second pairs of restriction rollers 50 according to this embodiment (two pairs in the example shown in FIG. 2A) are disposed in the conveyance direction (X-direction) of the pipe P.

The holding member 60 (member to which hatching has been applied in FIG. 2A) is connected to the first pair of restriction rollers 40, the second pair of restriction rollers 50, and the yoke member 30, and integrally holds the first pair of restriction rollers 40, the second pair of restriction rollers 50, and the yoke member 30. The holding member 60 according to this embodiment also functions to press the member pieces 30a and 30b (see FIG. 2A) from a facing direction of the member pieces (vertical direction in this embodiment) to integrally form the member pieces 30a and 30b.

To the holding member 60, a known linear stage (not shown) or gonio stage (not shown) is attached in a part denoted by the reference 61, and the holding member is movable in parallel in a first direction (Y-direction shown in FIG. 2A; horizontal direction in this embodiment) perpendicular to the conveyance direction (X-direction) of the pipe P, movable in parallel in a second direction (Z-direction shown in FIG. 2A; vertical direction in this embodiment) perpendicular to both of the conveyance direction (X-direction) of the pipe P and the first direction (Y-direction), rotatable around the first direction (Y-direction), and rotatable around the second direction (Z-direction). Specifically, the holding member 60 is connected to a base member 62 fixed to the conveyance line via the linear stage enabling the parallel movement in each of the directions described above or the gonio stage enabling the rotation along each of the directions described above.

The guide roller group 70 is positioned on the upstream side in a conveyance direction (X-direction) of a pipe P with respect to the first pair of restriction rollers 40, and two or more pairs of guide rollers 71 (four pairs in the examples shown in FIGS. 2A and 7A) in which the guide rollers are disposed to face each other with a gap interposed therebetween are disposed in the conveyance direction of the pipe P. In the examples shown in FIGS. 2A and 7A, guide rollers 71a and 71b constituting the pair of guide rollers 71 are disposed to face each other in the vertical direction. However, the invention is not limited thereto, and the rollers may be disposed to face each other in another direction such as a horizontal direction. In addition, as in a modified example shown in FIG. 8, pairs of guide rollers 71 in which the facing direction is shifted by 90° may be alternately disposed in the conveyance direction of the pipe P, such that a pair of guide rollers 71 (71A) disposed to face each other in the vertical direction and a pair of guide rollers 71 (71B) disposed to face each other in the horizontal direction are alternately disposed.

In addition, as shown in FIG. 7C, each of the guide rollers 71a and 71b constituting the pair of guide rollers 71 according to this embodiment is a grooved roller, and a substantially circular groove which is formed by the guide rollers 71a and 71b corresponds to the above-described gap. The guide roller group 70 functions to guide a pipe P passing through the gap (groove) to the first pair of restriction rollers 40. The size (diameter R of the groove) of the gap of the respective pairs of guide rollers 71 constituting the guide roller group 70 is larger than the size (diameter r of the groove) of the gap of the first pair of restriction rollers 40, and the closer the pair of guide rollers is to the first pair of restriction rollers 40, the smaller the gap is.

As described above, the device of detecting magnetic characteristic change 100 according to this embodiment is provided with the first pair of restriction rollers 40 and the second pair of restriction rollers 50 as a preferable configuration of the feeding mechanism. Therefore, in a case where the positional relationship among the first pair of restriction rollers 40, the second pair of restriction rollers 50, and the yoke member 30 is appropriately set, it is possible to avoid the collision of the pipe P with the yoke member 30 and to suppress the positional variation of the pipe P in the yoke member 30 interposed between the first pair of restriction rollers 40 and the second pair of restriction rollers 50. Appropriately setting the positional relationship is that for example, the center of the gap of the first pair of restriction rollers 40, the center of the first opening portion 31, the center of the second opening portion 32, and the center of the second pair of restriction rollers 50 are set to be positioned on one straight line.

The device of detecting magnetic characteristic change 100 according to this embodiment is provided with the holding member 60 as a preferable configuration of the feeding mechanism. Therefore, in a case where a curved pipe P is restricted by the first pair of restriction rollers 40, and then the first pair of restriction rollers 40 are pressed from the pipe P with the variation in the position or direction of the pipe P, the holding member 60 holding the first pair of restriction rollers 40 is at least moved in parallel or rotated in accordance with the variation in the position or direction of the pipe P. With this, since the first pair of restriction rollers 40, the second pair of restriction rollers 50, and the yoke member 30 are at least moved in parallel or rotated integrally, the positional relationship among the first pair of restriction rollers 40, the second pair of restriction rollers 50, and the yoke member 30 is maintained. Accordingly, even in a case where the pipe P is largely curved, and thus the first pair of restriction rollers 40 is moved in parallel or rotated, it is possible to avoid the collision of the pipe P with the yoke member 30. In addition, it is possible to suppress the positional variation of the pipe P in the yoke member 30 interposed between the first pair of restriction rollers 40 and the second pair of restriction rollers 50 and to improve axial symmetry of the magnetic circuit formed by the pipe P and the yoke member 30.

Furthermore, the device of detecting magnetic characteristic change 100 according to this embodiment is provided with the guide roller group 70 as a preferable configuration of the feeding mechanism. Accordingly, as in this embodiment, the size of the gap of the pair of guide rollers 71 farthest from the first pair of restriction rollers 40 can be set to a large value even in a case where the size of the gap of the first pair of restriction rollers 40 is set to be substantially the same as the outer diameter of the pipe P to suppress the positional variation of the pipe P in the yoke member 30 interposed between the first pair of restriction rollers 40 and the second pair of restriction rollers 50 as much as possible. Accordingly, it is possible to allow a front end section of the pipe P to easily pass through the gap of the above farthest pair of guide rollers 71 even in a case where the pipe P is largely curved. In addition, the closer the pair of guide rollers 71 is to the first pair of restriction rollers 40, the smaller the size of the gap is, and thus it is possible to allow a front end section of the pipe P to be stably guided to and to pass through the gap of the first pair of restriction rollers 40.

Figure 8:
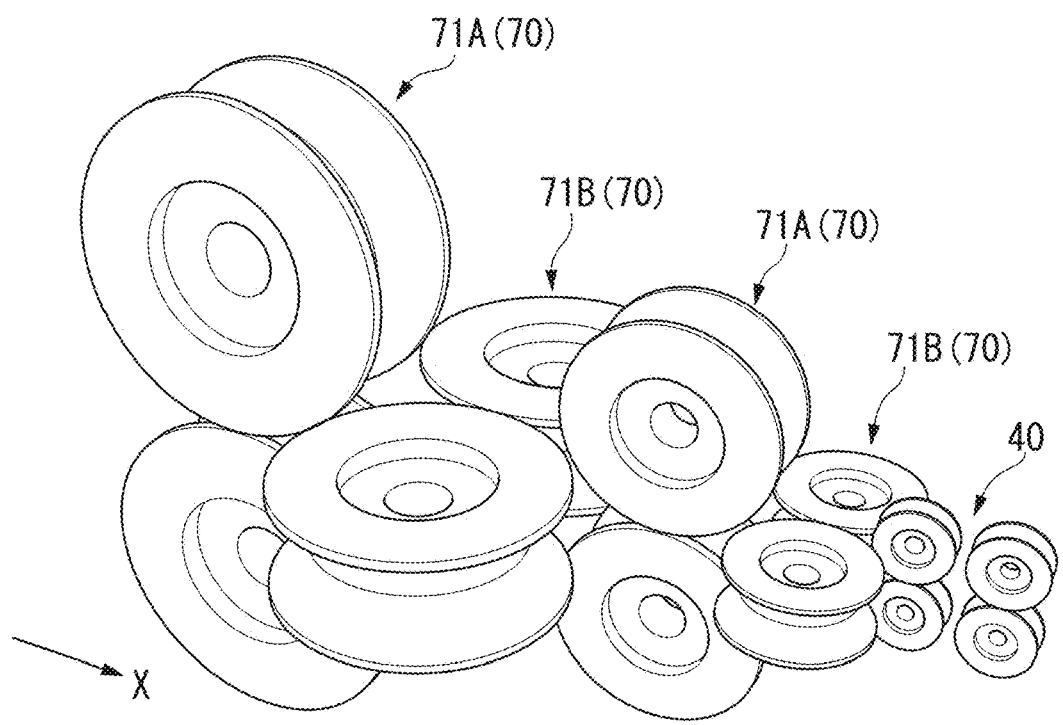
FIG. 8 is a perspective view schematically showing a configuration of a feeding mechanism according to a modified example of the embodiment.

Particularly, according to the guide roller group of the feeding mechanism according to the modified example shown in FIG. 8, a distance (distance in the conveyance direction of the pipe P) between the neighboring pairs of guide rollers 71A and 71B can be reduced as compared to a case where the facing directions of the pairs of guide rollers 71 neighboring in the conveyance direction of the pipe P are the same (examples shown in FIGS. 2A and 7A). Therefore, it is possible to smoothly deliver the pipe P from one pair of guide rollers 71A to the other pair of guide rollers 71B.

Hereinafter, a method (including a predetermined procedure which is executed by the detector 80) of detecting portions where magnetic characteristics change using the device of detecting magnetic characteristic change 100 having the above-described configuration will be described.

Figure 9:
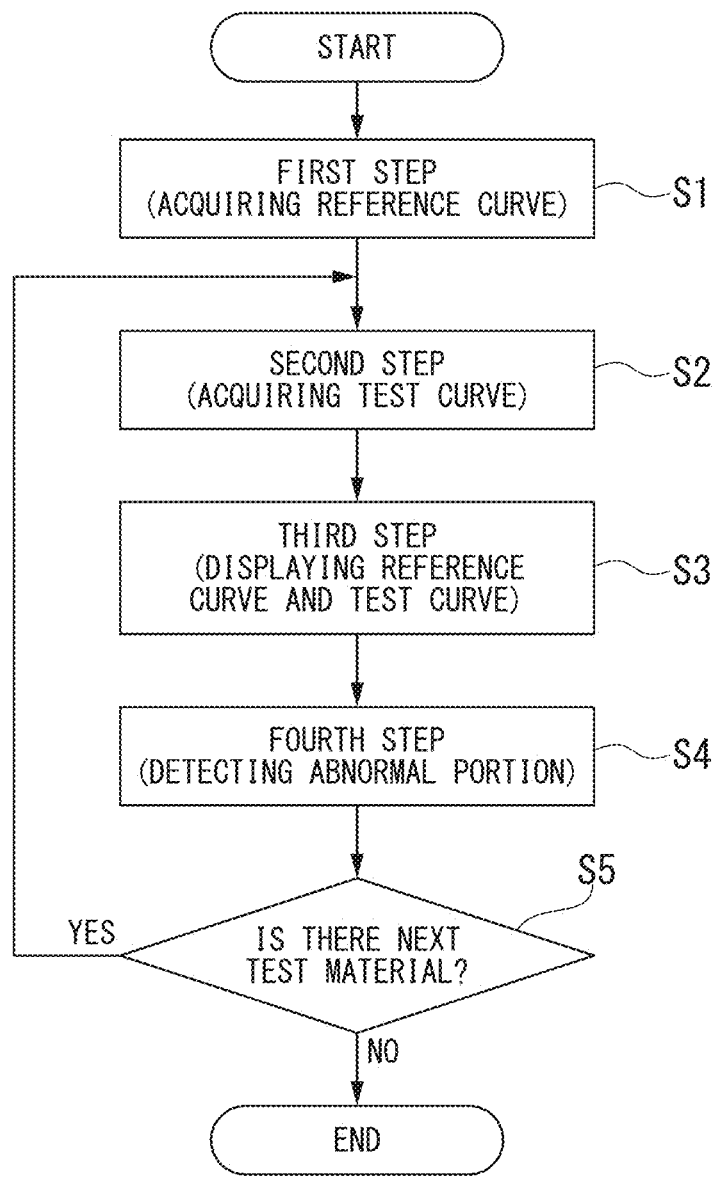
FIG. 9 is a flowchart schematically showing steps of a method of detecting portions where magnetic characteristics change according to the embodiment.

FIG. 9 is a flowchart schematically showing steps of the method of detecting portions where magnetic characteristics change according to this embodiment.

As shown in FIG. 9, in the method of detecting portions where magnetic characteristics change according to this embodiment, first, a first step in which a reference material is prepared, a magnetic characteristic curve is acquired by magnetizing the reference material with the device of detecting magnetic characteristic change 100, and the acquired magnetic characteristic curve is defined as a reference curve is executed (S1 in FIG. 9). Specifically, a triangular or sinusoidal wave exciting current is applied to the exciting coil 10 to magnetize the reference material, and the detector 80 calculates a field intensity based on the exciting current. By time-integrating the output voltage of the detecting coil 20, the magnitude and the density of the magnetic flux generated in the reference material are calculated. Accordingly, the detector 80 acquires a reference curve which is a magnetic characteristic curve with a vertical axis indicating a magnetic flux density and a horizontal axis indicating an exciting current (proportional to the field intensity). The detector 80 stores the acquired reference curve.

Next, in the method of detecting portions where magnetic characteristics change according to this embodiment, a second step in which a magnetic characteristic curve is acquired by magnetizing a test material which is a test target pipe P by the device of detecting magnetic characteristic change 100 under the same conditions as in the first step, and the acquired magnetic characteristic curve is defined as a test curve is executed (S2 in FIG. 9). Specifically, an exciting current having the same frequency and amplitude as in the case of the magnetization of the reference material is applied to the exciting coil 10 to magnetize the test material, and the detector 80 calculates a field intensity based on the exciting current. By time-integrating the output voltage of the detecting coil 20, the magnitude and the density of the magnetic flux generated in the test material are calculated. Accordingly, the detector 80 acquires a test curve which is a magnetic characteristic curve with a vertical axis indicating a magnetic flux density and a horizontal axis indicating an exciting current.

Next, in the method of detecting portions where magnetic characteristics change according to this embodiment, a third step in which the reference curve and the test curve are simultaneously displayed in the same orthogonal coordinate system (the vertical axis indicates a magnetic flux density, and the horizontal axis indicates an exciting current) is executed (S3 in FIG. 9). Specifically, the detector 80 simultaneously displays the reference curve and the test curve on a monitor thereof.

Figure 10:
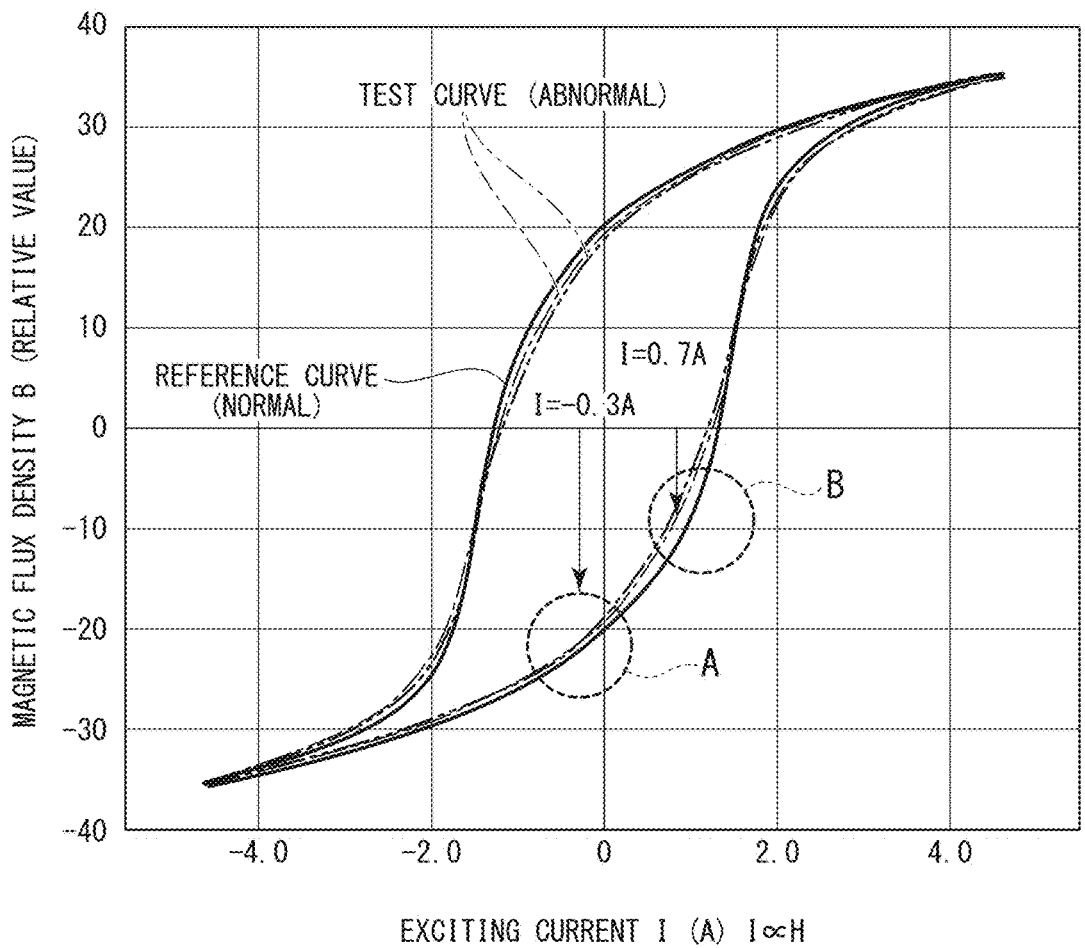
FIG. 10 is a graph schematically showing an example of a reference curve and a test curve displayed by a detector according to the embodiment.

FIG. 10 is a view schematically showing an example of the reference curve and the test curve displayed by the detector 80. The reference curve and the test curve are acquired by exciting both a reference material and a test material with a triangular-wave exciting current of 0.1 Hz with the use of, as the test material, a pipe P in which the Vickers hardness of a region which is approximately 12% of a cross-sectional area is reduced by 100 Hv or greater (normal portion: 300 Hv, abnormal portion: less than 200 Hv). In FIG. 10, the curves represented by the dashed-dotted line and the dashed-two dotted line are test curves (abnormal), and the curves represented by the solid line are reference curves (normal).

As shown in FIG. 10, a slight significant difference is generated mainly between the shapes of the magnetic characteristic curves in a case where there is an abnormal portion in the pipe P (test curve) and in a case where there is no abnormal portion (reference curve).

In FIG. 10, the point represented by the reference A is a point at which the rate of change of the inclination of a tangent of the magnetic characteristic curve in a case where there is an abnormal portion reaches the maximum, that is, a point at which the amplitude of the Barkhausen noise reaches the maximum. In addition, in FIG. 10, the point represented by the reference B is a point at which the rate of change of the inclination of a tangent of the magnetic characteristic curve in a case where there is no abnormal portion reaches the maximum. As shown in FIG. 10, at the point at which the amplitude of the Barkhausen noise reaches the maximum, or in the rotating magnetization region, the reference curve and the test curve have substantially the same shape, and a significant difference is not generated.

Next, in the method of detecting portions where magnetic characteristics change according to this embodiment, a fourth step in which an abnormal portion in the test material is detected based on the difference in the shape between the reference curve and the test curve is executed (S4 in FIG. 9). Specifically, the shapes of the reference curve and the test curve displayed on the monitor of the detector 80 as shown in FIG. 10 are visually observed by an operator to recognize a slight difference in the shape between the magnetic characteristic curves, and in accordance with the magnitude of the difference in the shape, an abnormal portion in the test material can be accurately detected.

Here, according to the results of the intensive studies of the inventors, it has been found that in the above-described fourth step, the difference in the shape between the reference curve and the test curve that is used to detect an abnormal portion in the test material is actualized by a difference between a change of the inclination of the tangent of the reference curve (corresponding to a change of the differential magnetic permeability) and a change of the inclination of the tangent of the test curve (corresponding to a change of the differential magnetic permeability).

Accordingly, in the above-described fourth step, an abnormal portion in the test material is preferably detected based on a difference between a change of the inclination of the tangent of the reference curve and a change of the inclination of the tangent of the test curve. In this preferable method, for example, a configuration may be employed in which the detector 80 simultaneously displays the change of the inclination of the tangent of the reference curve and the change of the inclination of the tangent of the test curve in the same orthogonal coordinate system with a vertical axis indicating a magnitude of the change and a horizontal axis indicating an exciting current on the monitor. An abnormal portion in the test material can be detected by visually observing the display by an operator.

In addition, in a case where a triangular or sinusoidal wave exciting current is applied to the exciting coil 10 as in this embodiment, the inclination (differential magnetic permeability) of a tangent of the magnetic characteristic curve is correlated with the output voltage of the detecting coil 20. Particularly, in a case where the exciting current is a triangular wave, the differential magnetic permeability is proportional to the output voltage of the detecting coil 20. Hereinafter, this will be described.

In a case where an exciting current I is a triangular wave, a time differential value dI/dt of an exciting current I is constant. Accordingly, Formula (1) is satisfied.

$$dI/dt = C1 \text{ (C1 is a constant)} \tag{1}$$

In addition, since a field intensity H of the magnetic field generated by the exciting coil 10 is proportional to the exciting current I applied to the exciting coil 10, Formula (2) is satisfied.

$$H = C2 \cdot I \text{ (C2 is a constant)} \tag{2}$$

Formula (3) is satisfied by Formulae (1) and (2).

$$dt/dH = 1/(C1 \cdot C2) \tag{3}$$

A magnetic flux $\phi$ generated in the pipe P (reference material and test material) and a magnetic flux density B has a relationship represented by Formula (4) with S indicating a cross-sectional area of the pipe P.

$$B = \phi/S \tag{4}$$

Here, Formula (5) is satisfied with $\mu$ indicating a differential magnetic permeability.

$$\mu = dB/dH = dt/dH \cdot dB/dt \tag{5}$$

In a case where Formula (3) is substituted in the right side of Formula (5), Formula (6) is satisfied.

$$\mu = 1/(C1 \cdot C2) \cdot dB/dt \tag{6}$$

In a case where Formula (4) is substituted in the right side of Formula (6), Formula (7) is satisfied.

$$\mu = 1/(C1 \cdot C2) \cdot d\phi/dt \cdot 1/S$$
$$= 1/(C1 \cdot C2 \cdot S) \cdot d\phi/dt \tag{7}$$

In Formula (7), $d\phi/dt$ is equal to the output voltage of the detecting coil 20. Accordingly, in a case where $d\phi/dt$ is represented by V and $1/(C1 \cdot C2 \cdot S)$ is represented by C3 (C3 is a constant), Formula (7) is represented by Formula (8).

$$\mu = C3 \cdot V \tag{8}$$

That is, in a case where an exciting current I is a triangular wave, the inclination (differential magnetic permeability $\mu$) of a tangent of the magnetic characteristic curve is proportional to an output voltage V of the detecting coil 20. Similarly, in a case where an exciting current I is a sinusoidal wave, the inclination (differential magnetic permeability $\mu$) of a tangent of the magnetic characteristic curve is correlated with an output voltage V of the detecting coil 20.

As above, since the inclination (differential magnetic permeability $\mu$) of a tangent of the magnetic characteristic curve is correlated with an output voltage V of the detecting coil 20, a change of the inclination of a tangent of the magnetic characteristic curve (reference curve and test curve) can be recognized by time-differentiating the output voltage of the detecting coil 20. In other words, an abnormal portion in the test material can be detected by calculating a time differential value of the output voltage of the detecting coil 20, instead of directly calculating a change of the inclination of a tangent of the magnetic characteristic curve.

That is, in the above-described fourth step, based on a difference between the time differential value of the output voltage of the detecting coil 20 obtained regarding the reference material and the time differential value of the output voltage of the detecting coil 20 obtained regarding the test material, an abnormal portion in the test material can be detected.

In the above-described preferable method, for example, a configuration may be employed in which the detector 80 simultaneously displays the time differential value of the output voltage of the detecting coil 20 obtained regarding the reference material and the time differential value of the output voltage of the detecting coil 20 obtained regarding the test material in the same orthogonal coordinate system with a vertical axis indicating a time differential value of the output voltage of the detecting coil 20 and a horizontal axis indicating a time on the monitor. An abnormal portion in the test material can be detected by visually observing the display by an operator.

Figure 11:
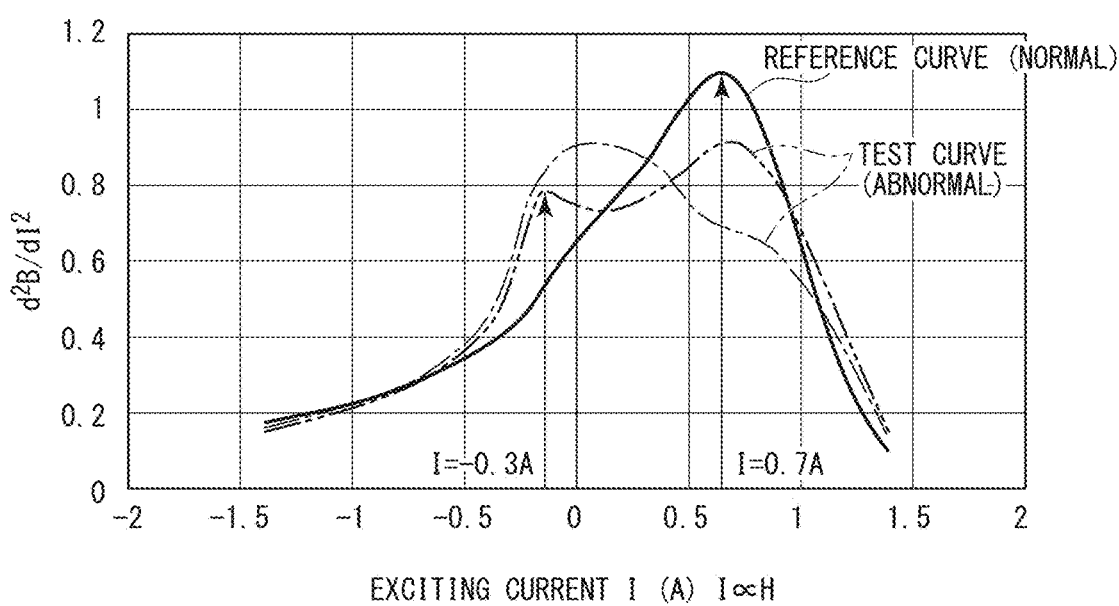
FIG. 11 is a graph showing the relationship between an exciting current and a change of the inclination of a tangent of the reference curve and the test curve shown in FIG. 10.

FIG. 11 is a graph showing the relationship between the exciting current and the change of the inclination of the tangent of the reference curve and the test curve shown in FIG. 10. Specifically, FIG. 11 shows the relationship between the exciting current and $d^2B/dI^2$ (a value obtained by second-order differentiating the magnetic flux density B by the exciting current I) calculated from the induced electromotive force generated in the detecting coil 20.

In the above example, in the fourth step, any one of the following (a) to (c) is simultaneously displayed in the same orthogonal coordinate system on the monitor of the detector 80, and this display is visually observed by an operator to detect an abnormal portion in the test material.

(a) Reference curve and test curve (b) Change of inclination of tangent of reference curve and change of inclination of tangent of test curve (c) Time differential value of output voltage of detecting coil 20 obtained regarding reference material and time differential value of output voltage of detecting coil 20 obtained regarding test material However, the abnormal portion detecting method according to this embodiment is not limited thereto, and in the fourth step, the detector 80 may automatically detect an abnormal portion, instead of or in addition to the judgement by visual observation by an operator. That is, a configuration can also be employed in which the detector 80 performs a procedure for automatically detecting an abnormal portion in the test material based on a difference in the shape between the reference curve and the test curve.

Examples of the procedure for automatically detecting an abnormal portion in the test material by the detector 80 include a procedure for automatically detecting an abnormal portion in the test material in accordance with the magnitude of the change of the inclination of the tangent of each magnetic characteristic curve at a field intensity within a predetermined range.

In addition, for example, a procedure for automatically detecting an abnormal portion in the test material in accordance with the magnitude of a time differential value of the output voltage of the detecting coil 20 obtained regarding the pipe P (reference material and test material) for a predetermined period of time can also be employed.

Figure 12:
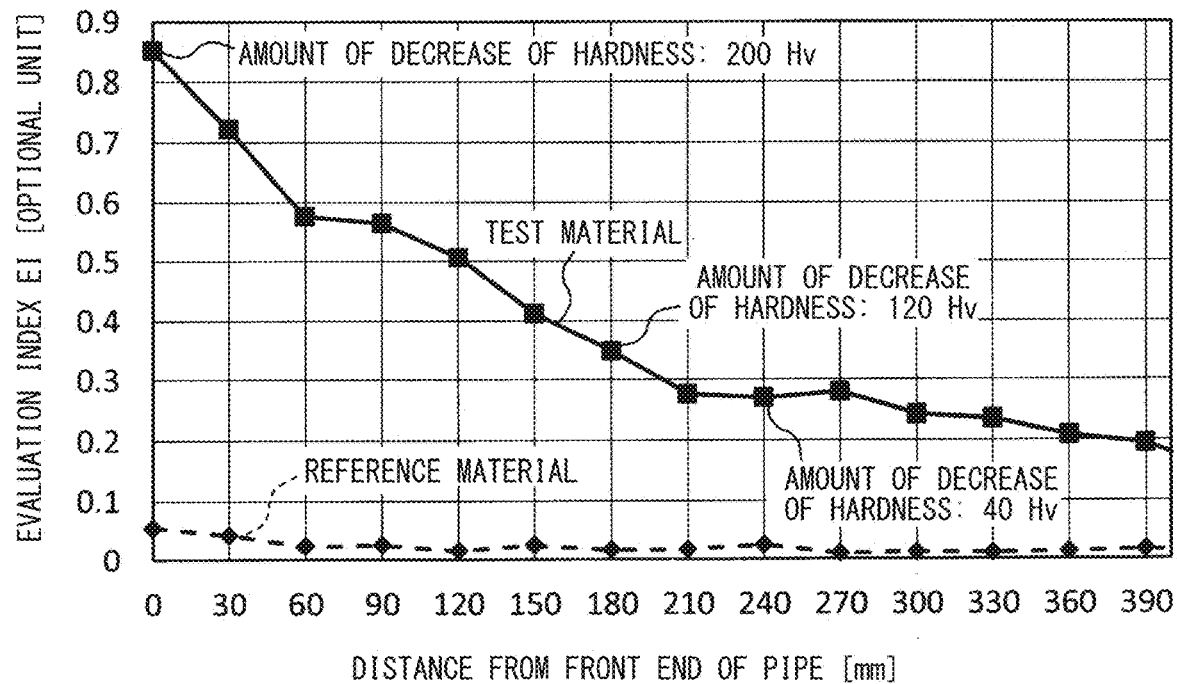
FIG. 12 is a view showing an example of results of the calculation of an evaluation index regarding a reference material and a test material having an abnormal portion in which the amount of decrease of Vickers hardness is gradually reduced from a pipe end.

FIG. 12 is a view showing an example of the results of the calculation of an evaluation index EI regarding a reference material and a test material having an abnormal portion in which the amount of decrease of Vickers hardness is gradually reduced from a pipe end (that is, the difference in the Vickers hardness between a normal portion and the abnormal portion is reduced).

As shown in FIG. 12, there is a significant difference between an evaluation index EI calculated regarding the reference material and an evaluation index EI calculated regarding the test material, and for example, in a case where a threshold value is set near an evaluation index EI=0.1, it can be automatically determined that the test material has an abnormal portion in a case where the calculated evaluation index EI exceeds the threshold value.

It is also thought that a plurality of different threshold values are set, and the level of an abnormal portion (the difference in the hardness between a normal portion and the abnormal portion) can be evaluated based on which threshold the evaluation index has exceeded.

In the method of detecting portions where magnetic characteristics change according to this embodiment, after the above-described fourth step is executed (S4 in FIG. 9), it is determined whether there is the next test material which can be tested using the same reference material (S5 in FIG. 9). In a case where there is the next test material ("Yes" in S5 in FIG. 9), the operation is executed again from the second step, and in a case where there is no next test material ("No" in S5 in FIG. 9), the operation is finished.

EXAMPLES

Hereinafter, an example of results obtained by inspecting a normal pipe and a pipe having portions where magnetic characteristics change using the device of detecting magnetic characteristic change 100 according to this embodiment under the following conditions (1) to (11) will be described.

Pipes P as inspection targets are eight pipes made of 0.15% carbon steel. In one of them, magnetic characteristic was changed by forcibly forming a poorly quenched portion by partially changing a cooling condition.

Figure 13:
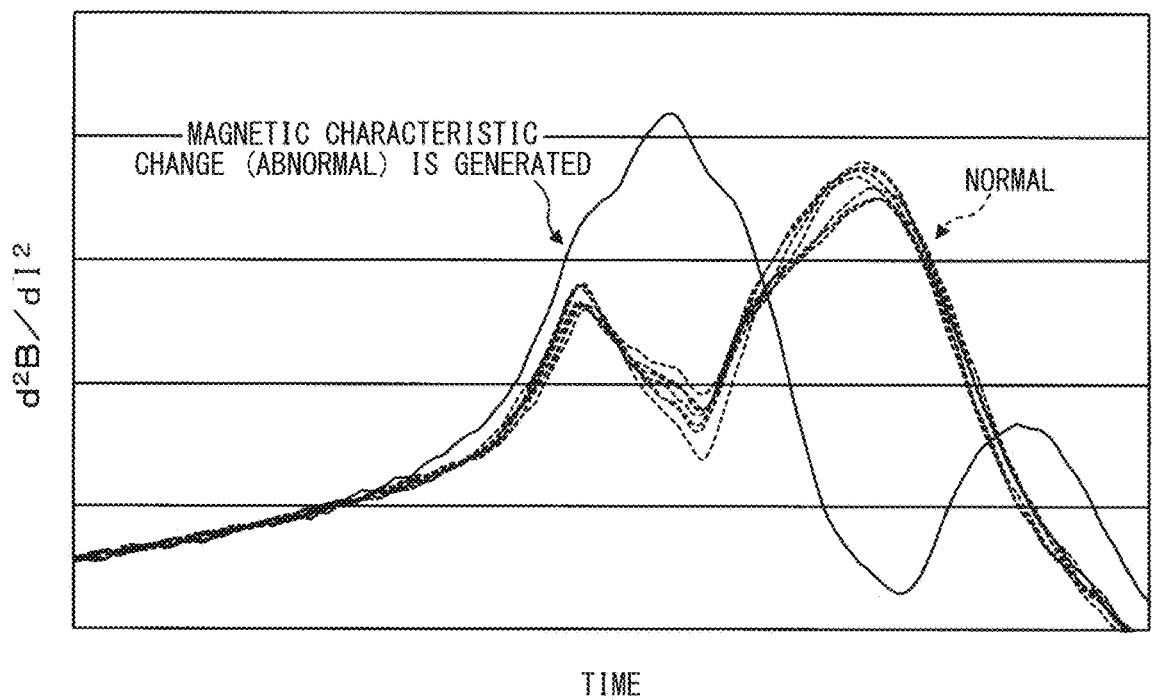
FIG. 13 is a graph showing an example of an inspection test which is performed by an inspection performed using the device of detecting magnetic characteristic change shown in FIG. 2A.

(1) Pipe Size: outer diameter 35 mm, thickness 3.5 mm
(2) Pipe Conveyance Speed: 300 mm/sec
(3) Material of Yoke Member 30: ultralow carbon steel having carbon concentration of 0.05%
(4) Size of Yoke Member 30: spherical shape having outer diameter of 160 mm and thickness of 30 mm
(5) Minimum Gap between Yoke Member 30 and Outer Surface of Pipe: 10 mm
(6) Size of Exciting Coil 10: inner diameter 58 mm, length 95 mm
(7) Size of Detecting Coil 20: inner diameter 56 mm, length 10 mm
(8) Number of Windings of Exciting Coil 10: 200
(9) Number of Windings of Detecting Coil 20: 30
(10) Excitation Current: triangular wave with peak current of 12 A
(11) Excitation Frequency: 1.5 Hz FIG. 13 shows an example of inspection results obtained by the above inspection. In FIG. 13, the horizontal axis indicates a time representing a magnetization cycle, and the vertical axis indicates $d^2B/dI^2$ (value obtained by second-order differentiating the magnetic flux density B by the exciting current I) calculated from the induced electromotive force generated in the detecting coil 20. As shown in FIG. 13, the waveform related to one pipe having portions where magnetic characteristics change is obviously different from waveforms related to other seven normal pipes. Accordingly, the portions where magnetic characteristics change can be detected from the difference in the waveform.

Figure 14:
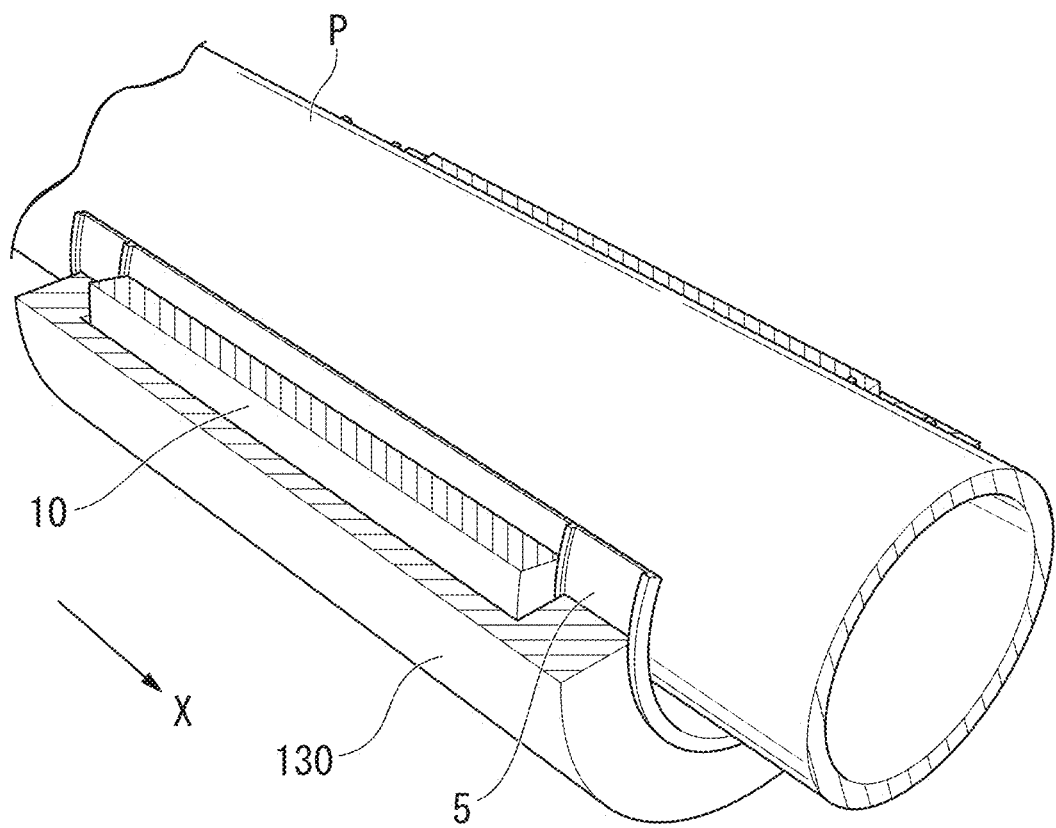
FIG. 14 is a perspective view schematically showing configurations of an exciting coil, a bobbin, and a yoke member according to a modified example of the embodiment.

Another embodiment will be described. In the above-described examples, the yoke member has a spherical shape. However, in this embodiment, a cylindrical yoke member 130 can also be employed as shown in FIG. 14. The sizes of the yoke member 130 and a pipe P according to this embodiment are as follows.

(1) Length of Yoke Member 130 in X-direction Shown in FIG. 14: 300 mm
(2) Size of Pipe P: outer diameter 115 mm, thickness 8.6 mm In the above-described embodiment, a poorly quenched portion is used as an example of portions where magnetic characteristics change which is a detection target. However, the detection target of the device of detecting magnetic characteristic change 100 according to the above-described embodiment is not limited thereto, and a change in the magnetic characteristic can be widely detected. For example, since carburizing or decarburizing is also associated with a change in the magnetic characteristics, it can be similarly detected.

INDUSTRIAL APPLICABILITY

According to the invention, it is possible to provide a device and a method of detecting magnetic characteristic change for a long material, which can reduce a dead zone of an end portion of the long material in a longitudinal direction and can accurately detect portions where magnetic characteristics change over the whole length thereof. Accordingly, the invention has very high industrial applicability.

EXPLANATION OF REFERENCES

5: BOBBIN
10: EXCITING COIL
20: DETECTING COIL
30, 130, 230: YOKE MEMBER
31: FIRST OPENING PORTION
32: SECOND OPENING PORTION
40: FIRST PAIR OF RESTRICTION ROLLERS
50: SECOND PAIR OF RESTRICTION ROLLERS
60: HOLDING MEMBER
70: GUIDE ROLLER GROUP
100: DEVICE OF DETECTING MAGNETIC CHARACTERISTIC CHANGE
P: PIPE

What is claimed is:

1. A device of detecting magnetic characteristic change for a long material which detects portions where magnetic characteristics change in the long material, comprising:
   an exciting coil into which the long material is inserted and which magnetizes the long material in a longitudinal direction;
   a detecting coil into which the long material is inserted and which detects a magnetic flux generated in the long material due to magnetization by the exciting coil; and
   a yoke member which has a first opening portion which is positioned on one side of the long material in the longitudinal direction and into which the long material is inserted and a second opening portion which is positioned on the other side of the long material in the longitudinal direction and into which the long material is inserted, and has a shape which is substantially axially symmetrical about an axis passing the first opening portion and the second opening portion, wherein the exciting coil and the detecting coil are surrounded by the yoke member, the first opening portion, and the second opening portion, and the first opening portion and the second opening portion are closer to the long material than a portion near the center of the yoke member.

2. The device of detecting magnetic characteristic change for a long material according to claim 1, wherein a minimum cross-sectional area of the yoke member is equal to or greater than that of the long material when viewed from a cross-section perpendicular to a direction in which the magnetic flux flows.

3. The device of detecting magnetic characteristic change for a long material according to claim 1, wherein a plurality of the detecting coils are provided, and at least one of the detecting coils is provided at at least one of the position of the first opening portion and the position of the second opening portion.

4. The device of detecting magnetic characteristic change for a long material according to claim 1, further comprising:

a feeding mechanism which relatively moves the long material in the longitudinal direction with respect to the exciting coil, the detecting coil, and the yoke member.

5. The device of detecting magnetic characteristic change for a long material according to claim 1, further comprising:

a detector which detects the portions where magnetic characteristics change based on an output voltage of the detecting coil, wherein the detector previously stores, as a reference curve, a magnetic characteristic curve acquired based on an output voltage of the detecting coil in a case where a reference material which is a long material having predetermined hardness is magnetized by the exciting coil. and the detector executes a procedure for acquiring a magnetic characteristic curve which is a test curve based on an output voltage of the detecting coil in a case where a test material which is a long test target material is magnetized by the exciting coil, a procedure for simultaneously displaying the reference curve and the test curve in the same orthogonal coordinate system, and a procedure for detecting the portions where magnetic characteristics change in the test material based on a difference in the shape between the reference curve and the test curve.

6. The device of detecting magnetic characteristic change for a long material according to claim 5, wherein the detector detects the portions where magnetic characteristics change in the test material based on a difference between a change of an inclination of a tangent of the reference curve and a change of an inclination of a tangent of the test curve.

7. The device of detecting magnetic characteristic change for a long material according to claim 6, wherein the detector detects the portions where magnetic characteristics change in the test material based on a difference between a time differential value of an output voltage of the detecting coil obtained regarding the reference material and a time differential value of an output voltage of the detecting coil obtained regarding the test material.

8. The device of detecting magnetic characteristic change for a long material according to claim 5, which is positioned in a rear stage of quenching of the long material.

9. A method of detecting magnetic characteristic change for a long material which detects portions where magnetic characteristics change in the long material using the device of detecting magnetic characteristic change for a long material according to claim 1, comprising:

a first step in which a long material having predetermined hardness is prepared as a reference material, a magnetic characteristic curve is acquired by magnetizing the reference material, and the acquired magnetic characteristic curve is defined as a reference curve;

a second step in which a magnetic characteristic curve is acquired by magnetizing a test material which is a long test target material under the same conditions as in the first step, and the acquired magnetic characteristic curve is defined as a test curve;

a third step in which the reference curve and the test curve are simultaneously displayed in the same orthogonal coordinate system; and a fourth step in which the portions where magnetic characteristics change in the test material are detected based on a difference in the shape between the reference curve and the test curve.

10. The method of detecting magnetic characteristic change for a long material according to claim 9, wherein in the fourth step, the portions where magnetic characteristics change in the test material are detected based on a difference between a change of an inclination of a tangent of the reference curve and a change of an inclination of a tangent of the test curve.

11. The method of detecting magnetic characteristic change for a long material according to claim 10, wherein in the first step, the reference material is inserted into the exciting coil and the detecting coil to magnetize the reference material by the exciting coil in a longitudinal direction, and a magnetic flux generated in the reference material due to magnetization by the exciting coil is detected by the detecting coil to acquire the reference curve, in the second step, the test material is inserted into the exciting coil and the detecting coil to magnetize the test material by the exciting coil in a longitudinal direction, and a magnetic flux generated in the test material due to magnetization by the exciting coil is detected by the detecting coil to acquire the test curve, and in the fourth step, the portions where magnetic characteristics change in the test material are detected based on a difference between a time differential value of an output voltage of the detecting coil obtained regarding the reference material and a time differential value of an output voltage of the detecting coil obtained regarding the test material.

12. The device of detecting magnetic characteristic change for a long material according to claim 2, wherein a plurality of the detecting coils are provided, and at least one of the detecting coils is provided at at least one of the position of the first opening portion and the position of the second opening portion.

13. The device of detecting magnetic characteristic change for a long material according to claim 2, further comprising:

a feeding mechanism which relatively moves the long material in the longitudinal direction with respect to the exciting coil, the detecting coil, and the yoke member.

14. The device of detecting magnetic characteristic change for a long material according to claim 3, further comprising:

a feeding mechanism which relatively moves the long material in the longitudinal direction with respect to the exciting coil, the detecting coil, and the yoke member.

15. The device of detecting magnetic characteristic change for a long material according to claim 2, further comprising:
- a detector which detects the portions where magnetic characteristics change based on an output voltage of the detecting coil,
- wherein the detector previously stores, as a reference curve, a magnetic characteristic curve acquired based on an output voltage of the detecting coil in a case where a reference material which is a long material having predetermined hardness is magnetized by the exciting coil, and
- the detector executes a procedure for acquiring a magnetic characteristic curve which is a test curve based on an output, voltage of the detecting coil in a case where a test material which is a long test target material is magnetized by the exciting coil, a procedure for simultaneously displaying the reference curve and the test curve in the same orthogonal coordinate system, and a procedure for detecting the portions where magnetic characteristics change in the test material based on a difference in the shape between the reference curve and the test curve.

16. The device of detecting magnetic characteristic change for a long material according to claim 3, further comprising:
- a detector which detects the portions where magnetic characteristics change based on an output voltage of the detecting coil,
- wherein the detector previously stores, as a reference curve, a magnetic characteristic curve acquired based on an output voltage of the detecting coil in a case where a reference material which is a long material having predetermined hardness is magnetized by the exciting coil, and
- the detector executes a procedure for acquiring a magnetic characteristic curve which is a test curve based on an output voltage of the detecting coil in a case where a test material which is a long test target material is magnetized by the exciting coil, a procedure for simultaneously displaying the reference curve and the test curve in the same orthogonal coordinate system, and a procedure for detecting the portions where magnetic characteristics change in the test material based on a difference in the shape between the reference curve and the test curve.

17. The device of detecting magnetic characteristic change for a long material according to claim 4, further comprising:
- a detector which detects the portions where magnetic characteristics change based on an output voltage of the detecting coil,
- wherein the detector previously stores, as a reference curve, a magnetic characteristic curve acquired based on an output voltage of the detecting coil in a case where a reference material which is a long material having predetermined hardness is magnetized by the exciting coil, and
- the detector executes a procedure for acquiring a magnetic characteristic curve which is a test curve based on an output, voltage of the detecting coil in a case where a test material which is a long test target material is magnetized by the exciting coil, a procedure for simultaneously displaying the reference curve and the test curve in the same orthogonal coordinate system, and a procedure for detecting the portions where magnetic characteristics change in the test material based on a difference in the shape between the reference curve and the test curve.

18. The device of detecting magnetic characteristic change for a long material according to claim 6, which is positioned in a rear stage of quenching of the long material.

19. The device of detecting magnetic characteristic change for a long material according to claim 7, which is positioned in a rear stage of quenching of the long material.

20. A method of detecting magnetic characteristic change for a long material which detects portions where magnetic characteristics change in the long material using the device of detecting magnetic characteristic change for a long material according to claim 2, comprising:
- a first step in which a long material having predetermined hardness is prepared as a reference material, a magnetic characteristic curve is acquired by magnetizing the reference material, and the acquired magnetic characteristic curve is defined as a reference curve;
- a second step in which a magnetic characteristic curve is acquired by magnetizing a test material which is a long test target material under the same conditions as in the first step, and the acquired magnetic characteristic curve is defined as a test curve;
- a third step in which the reference curve and the test curve are simultaneously displayed in the same orthogonal coordinate system; and
- a fourth step in which the portions where magnetic characteristics change in the test material are detected based on a difference in the shape between the reference curve and the test curve.

21. The device of detecting magnetic characteristic change for a long material according to claim 1, further comprising:
- a bobbin through which the long material passes,
- wherein the exciting coil and the detecting coil are wound around an outer surface of the bobbin, and
- portions forming the first opening portion and portions forming the second opening portion are fitting to grooves formed in end portions of the bobbin respectively.

* * * * *